United States Patent
Blaine et al.

(10) Patent No.: US 12,303,378 B2
(45) Date of Patent: May 20, 2025

(54) TENDON REPAIR SYSTEM

(71) Applicant: CATALYST ORTHOSCIENCE INC., Naples, FL (US)

(72) Inventors: Theodore Blaine, Old Greenwich, CT (US); Lee Kaback, Delmar, NY (US); Paul Sethi, Riverside, CT (US); Ephraim Akyuz, Salt Lake City, UT (US); Dale Davison, Naples, FL (US)

(73) Assignee: CATALYST ORTHOSCIENCE INC., Naples, FL (US)

( * ) Notice: Subject to any disclaimer, the term of this patent is extended or adjusted under 35 U.S.C. 154(b) by 324 days.

(21) Appl. No.: 17/961,217

(22) Filed: Oct. 6, 2022

(65) Prior Publication Data

US 2023/0106745 A1    Apr. 6, 2023

Related U.S. Application Data

(60) Provisional application No. 63/252,691, filed on Oct. 6, 2021.

(51) Int. Cl.
*A61F 2/08* (2006.01)
*A61B 17/04* (2006.01)

(52) U.S. Cl.
CPC ........ *A61F 2/0811* (2013.01); *A61B 17/0401* (2013.01); *A61B 2017/0404* (2013.01); *A61B 2017/0412* (2013.01); *A61B 2017/0448* (2013.01); *A61B 2017/0464* (2013.01);
(Continued)

(58) Field of Classification Search
CPC ............ A61F 2/0811; A61F 2002/0829; A61F 2002/087; A61F 2002/0882; A61B 17/0401; A61B 2017/0404; A61B 2017/0412; A61B 2017/0448; A61B 2017/0464
See application file for complete search history.

(56) References Cited

U.S. PATENT DOCUMENTS 9,381,019 B2 * 7/2016 Kubiak ................. A61F 2/0811
10,350,053 B2 * 7/2019 Kumar .................. A61F 2/0811
(Continued)

OTHER PUBLICATIONS

International Search Report dated Feb. 2, 2023 for corresponding PCT Application No. PCT/US2022/045890.

*Primary Examiner* — Tan-Uyen T Ho
*Assistant Examiner* — Khoa Tan Le
(74) *Attorney, Agent, or Firm* — David Meibos; Maywood IP Law

(57) ABSTRACT

A system for coupling a tendon to a bone may include a tendon coupling device engageable with a tendon, a fastener to secure the tendon coupling device to the tendon, a bone coupling device, and a flexible element. The flexible element may include a first portion and a second portion. The first portion of the flexible element may be couplable with the fastener to securably attach the flexible element to the tendon. The bone coupling device may include a bone-facing surface engageable with a surface of the bone proximate a bone tunnel formed through the bone, and a hole formed through the bone coupling device. The second portion of the flexible element may be receivable through the bone tunnel and the hole formed through the bone coupling device to engage an opposing surface of the bone coupling device and securably couple the tendon to the bone.

24 Claims, 28 Drawing Sheets

(52) U.S. Cl.
CPC . *A61F 2002/0829* (2013.01); *A61F 2002/087* (2013.01); *A61F 2002/0882* (2013.01)

(56) References Cited

U.S. PATENT DOCUMENTS

| | | | |
|---|---|---|---|
| 2005/0197699 A1* | 9/2005 | Jacobs | A61F 2/0811 623/13.14 |
| 2016/0008043 A1* | 1/2016 | Bonutti | A61B 17/0467 606/75 |

* cited by examiner

TENDON REPAIR SYSTEM

CROSS-REFERENCE TO RELATED APPLICATIONS

The present application claims the benefit of U.S. Provisional Patent Application No. 63/252,691, entitled TENDON REPAIR SYSTEM, which was filed on Oct. 6, 2021. The foregoing is incorporated by reference as though set forth herein in its entirety.

TECHNICAL FIELD

The present disclosure relates to medical devices, systems, methods, and instruments. More specifically, the present disclosure relates to medical devices, systems, methods, and instruments for securing tendons, ligaments, muscle, and/or other soft tissues to bone.

BACKGROUND

Tendon repair procedures are surgical procedures in which a separated tendon, ligament, muscle, and/or other soft tissues are reattached to bone.

Subscapularis repair is one example tendon repair procedure that may be performed during a shoulder arthroplasty procedure. A deltopectoral approach may be utilized during both an anatomic and a reverse shoulder arthroplasty procedure. In this approach, the subscapularis tendon may be detached from its insertion point on the lesser tubercle of the humerus by peeling the tendon, performing a tenotomy, and/or performing a lesser tuberosity osteotomy (LTO). Different methods, techniques, and implants exist for accomplishing a subscapularis repair following such detachment procedures. From a high level, subscapularis repair involves grasping the free or cut end of the subscapularis tendon and re-attaching it to the bone at or near its original attachment point. However, there is no general consensus for any specific technique that currently exists, and current techniques can be improved with regard to their complexity, time requirements, robustness, and/or repeatability.

Accordingly, improved tendon repair systems, devices, and methods that are more robust, secure, simple, and/or repeatable would be desirable to increase long term joint stability and help ensure a successful clinical outcome for the patient.

SUMMARY

The various devices, systems, methods, and instruments of the present disclosure have been developed in response to the present state of the art, and in particular, in response to the problems and needs in the art that have not yet been fully solved by currently available devices, systems, methods, and instruments for surgically repairing tendons. In some embodiments, the devices, systems, methods, and instruments of the present disclosure may provide improved surgical procedures for attaching tendons to bone.

In some embodiments, a system for coupling a tendon to a bone may include a tendon coupling device having a tendon-facing surface engageable with the tendon, a fastener configured to secure the tendon to the tendon coupling device, a bone coupling device, and a flexible element. The flexible element may include a first portion and a second portion. The first portion of the flexible element may be couplable with the fastener to securably attach the flexible element to the tendon. The bone coupling device may include a bone-facing surface engageable with a surface of the bone proximate a bone tunnel formed through the bone, an opposing surface, opposite the bone-facing surface, and a hole formed through the bone coupling device intermediate and passing through the bone-facing surface and the opposing surface of the bone coupling device. The second portion of the flexible element may be receivable through the bone tunnel and the hole to engage the opposing surface of the bone coupling device and securably couple the tendon to the bone.

In some embodiments of the system, the fastener may include a fastener shaft having a first end, a second end, and a longitudinal passageway formed through the fastener shaft intermediate the first end and the second end. The fastener may also include a first button coupled to the first end of the fastener shaft and a second button coupled to the second end of the fastener shaft. The fastener shaft may be configured to penetrate through the tendon and the tendon coupling device to secure the tendon coupling device to the tendon intermediate the first button and the second button, and the first portion of the flexible element may be receivable through the longitudinal passageway of the fastener shaft to securably attach the flexible element to the tendon.

In some embodiments of the system, the fastener may include a locking mechanism formed intermediate the fastener shaft and at least one of the first button and the second button. The locking mechanism may be configured to couplably secure the fastener shaft to at least one of the first button and the second button.

In some embodiments of the system, the fastener may include a curved fastener shaft having a leading end, a trailing end, a barbed feature coupled to the leading end, and a stop feature coupled to the trailing end. The barbed feature may be configured to penetrate through the tendon and the tendon coupling device to secure the tendon coupling device to the tendon intermediate the barbed feature and the stop feature. The first portion of the flexible element may be couplable with the fastener to securably attach the flexible element to the tendon.

In some embodiments of the system, the barbed feature may include a first barbed end, a second barbed end, and a gap formed intermediate the first barbed end and the second barbed end. In a first compressed state, the first barbed end and the second barbed end may be configured to compress toward each other. In a second expanded state, the first barbed end and the second barbed end may be configured to expand away from each other.

In some embodiments of the system, the tendon-facing surface may be a first tendon-facing surface. The tendon coupling device may also include a second tendon-facing surface, opposite the first tendon-facing surface. The tendon may be receivable between the first tendon-facing surface and the second tendon-facing surface of the tendon coupling device to secure the tendon to the tendon coupling device.

In some embodiments of the system, the bone coupling device may be integrally formed with the tendon coupling device.

In some embodiments, a system for coupling a tendon to a bone may include a tendon coupler having a tendon-facing surface engageable with the tendon, a first fastener configured to couple the tendon coupler to the tendon, a bone coupler coupled to the tendon coupler, the bone coupler having a bone-facing surface engageable with a surface of the bone, and a second fastener configured to secure the bone coupler to the surface of the bone to securably couple the tendon to the bone.

In some embodiments of the system, the first fastener may include a first portion of a flexible element, the second fastener may include a second portion of the flexible element, and the bone coupler may include an opposing surface opposite the bone-facing surface, and a hole formed through the bone coupler intermediate and passing through the bone-facing surface and the opposing surface of the bone coupler. The bone-facing surface of the bone coupler may be engageable with the surface of the bone proximate a bone tunnel formed through the bone. The first portion of the flexible element may be configured to secure the tendon coupler to the tendon, and the second portion of the flexible element may be configured to secure the bone coupler to the bone to secure the tendon to the bone.

In some embodiments of the system, the second fastener may include at least one of: a bone staple, a bone screw, a bone anchor, a wire, and a rivet.

In some embodiments of the system, the first fastener may include a fastener shaft having a first end, a second end, and a longitudinal passageway formed through the fastener shaft intermediate the first end and the second end. The first fastener may also include a first button coupled to the first end of the fastener shaft, and a second button coupled to the second end of the fastener shaft. The fastener shaft may be configured to penetrate through the tendon and the tendon coupler to secure the tendon coupler to the tendon intermediate the first button and the second button. A first portion of a flexible element may be receivable through the longitudinal passageway of the fastener shaft to securably attach the flexible element to the tendon.

In some embodiments of the system, the first fastener may include a curved fastener shaft having a leading end, a trailing end, a barbed feature coupled to the leading end, and a stop feature coupled to the trailing end. The barbed feature may be configured to penetrate through the tendon and the tendon coupler to secure the tendon coupler to the tendon intermediate the barbed feature and the stop feature. A first portion of a flexible element may be couplable with the first fastener to securably attach the flexible element to the tendon.

In some embodiments of the system, the second fastener may include at least one of: a bone staple, a bone screw, and a bone anchor.

In some embodiments of the system, the first fastener may include a fastener shaft having a first end, a second end, and a longitudinal passageway formed through the fastener shaft intermediate the first end and the second end. The first fastener may also include a first button coupled to the first end of the fastener shaft, and a second button coupled to the second end of the fastener shaft. The fastener shaft may be configured to penetrate through the tendon and the tendon coupler to secure the tendon coupler to the tendon intermediate the first button and the second button. A first portion of a flexible element may be receivable through the longitudinal passageway of the fastener shaft to securably attach the flexible element to the tendon.

In some embodiments of the system, the first fastener may include a curved fastener shaft having a leading end, a trailing end, a barbed feature coupled to the leading end, and a stop feature coupled to the trailing end. The barbed feature may be configured to penetrate through the tendon and the tendon coupler to secure the tendon coupler to the tendon intermediate the barbed feature and the stop feature. A first portion of a flexible element may be couplable with the first fastener to securably attach the flexible element to the tendon.

In some embodiments, a system for coupling a tendon to a bone may include a tendon connection device having a tendon-facing surface engageable with the tendon, a flexible element having a first portion and a second portion, and a bone connection device. The bone connection device may include a bone-facing surface engageable with a surface of the bone proximate a bone tunnel formed through the bone, an opposing surface opposite the bone-facing surface, and a hole formed through the bone connection device intermediate and passing through the bone-facing surface and the opposing surface. The first portion of the flexible element may be configured to couple the tendon connection device to the tendon, and the second portion of the flexible element may be receivable through the bone tunnel and the hole to engage the opposing surface of the bone connection device and securably couple the tendon to the bone.

In some embodiments of the system, the tendon connection device may include at least one of: a mesh, a web, a pledget, a pad, and a patch.

In some embodiments of the system, the first portion of the flexible element may be configured to weave around the tendon connection device and the tendon to secure the tendon connection device to the tendon.

In some embodiments of the system, the tendon-facing surface may be a first tendon-facing surface, the tendon connection device may also include a second tendon-facing surface opposite the first tendon-facing surface, and the tendon may be receivable between the first tendon-facing surface and the second tendon-facing surface of the tendon connection device to secure the tendon to the tendon connection device.

In some embodiments of the system, the tendon connection device may be configured to fold around the tendon, and the flexible element may be configured to penetrate through the tendon connection device and the tendon to secure the tendon connection device to the tendon.

In some embodiments of the system, the bone connection device may be integrally formed with the tendon connection device.

These and other features and advantages of the present disclosure will become more fully apparent from the following description and appended claims or may be learned by the practice of the systems, devices, and methods set forth herein.

BRIEF DESCRIPTION OF THE DRAWINGS

Exemplary embodiments of the present disclosure will become more fully apparent from the following description taken in conjunction with the accompanying drawings. Understanding that these drawings depict only exemplary embodiments and are, therefore, not to be considered limiting of the scope of the present disclosure, the exemplary embodiments of the present disclosure will be described with additional specificity and detail through use of the accompanying drawings in which.

Figure 1:
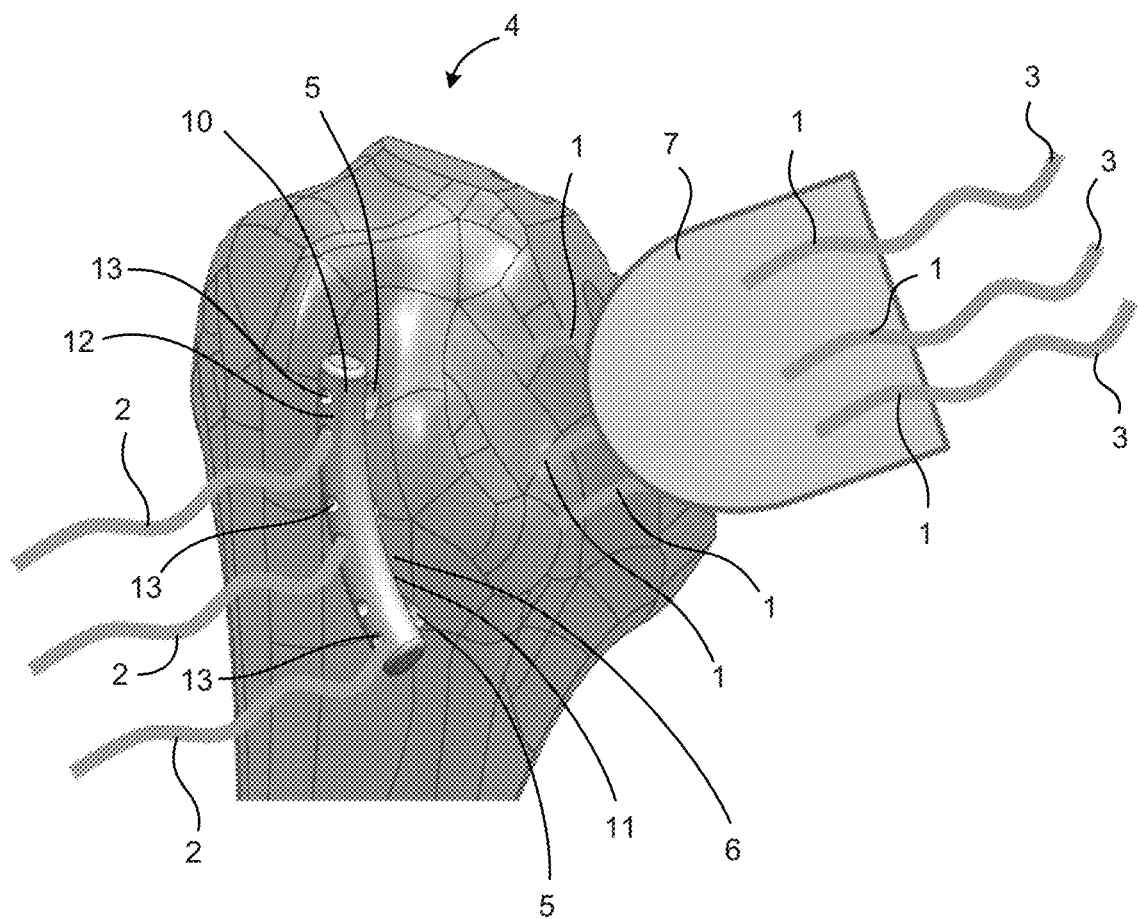
FIG. 1 illustrates a perspective side view of a tendon repair system, according to embodiments of the present disclosure.

It is to be understood that the drawings are for purposes of illustrating the concepts of the present disclosure and may not be drawn to scale. Furthermore, the drawings illustrate exemplary embodiments and do not represent limitations to the scope of the present disclosure.

DETAILED DESCRIPTION

Exemplary embodiments of the present disclosure will be best understood by reference to the drawings, wherein like parts are designated by like numerals throughout. It will be readily understood that the components of the present disclosure, as generally described and illustrated in the drawings, could be arranged, and designed in a wide variety of different configurations. Thus, the following more detailed description of the embodiments of the devices, systems, and methods, as represented in the drawings, is not intended to limit the scope of the present disclosure but is merely representative of exemplary embodiments of the present disclosure.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in the drawings, the drawings are not necessarily drawn to scale unless specifically indicated.

Standard medical planes of reference and descriptive terminology are employed in this specification. While these terms are commonly used to refer to the human body, certain terms are applicable to physical objects in general.

A standard system of three mutually perpendicular reference planes is employed. A sagittal plane divides a body into right and left portions. A coronal plane divides a body into anterior and posterior portions. A transverse plane divides a body into superior and inferior portions. A mid-sagittal, mid-coronal, or mid-transverse plane divides a body into equal portions, which may be bilaterally symmetric. The intersection of the sagittal and coronal planes defines a superior-inferior or cephalad-caudal axis. The intersection of the sagittal and transverse planes defines an anterior-posterior axis. The intersection of the coronal and transverse planes defines a medial-lateral axis. The superior-inferior or cephalad-caudal axis, the anterior-posterior axis, and the medial-lateral axis are mutually perpendicular.

Anterior means toward the front of a body. Posterior means toward the back of a body. Superior or cephalad means toward the head. Inferior or caudal means toward the feet or tail. Medial means toward the midline of a body, particularly toward a plane of bilateral symmetry of the body. Lateral means away from the midline of a body or away from a plane of bilateral symmetry of the body. Axial means toward a central axis of a body. Abaxial means away from a central axis of a body. Ipsilateral means on the same side of the body. Contralateral means on the opposite side of the body. Proximal means toward the trunk of the body. Proximal may also mean toward a user or operator. Distal means away from the trunk. Distal may also mean away from a user or operator. Dorsal means toward the top of the foot. Plantar means toward the sole of the foot. Varus means deviation of the distal part of the leg below the knee inward, resulting in a bowlegged appearance. Valgus means deviation of the distal part of the leg below the knee outward, resulting in a knock-kneed appearance.

As used herein, the term "fastener" may include any structure(s), device(s), or component(s) described or contemplated herein which may be utilized to couple two or more objects together.

As used herein, the phrases: "first portion", "second portion", "intermediate portion", etc., (and their analogs) are defined broadly to include any portion of the referenced structure(s), device(s), or component(s) that may be utilized to perform a specific function (e.g., coupling/fastening one object to another object, etc.).

Although the present disclosure describes tendon repair systems, devices, components, methods, and instruments in the context of subscapularis tendon repair for a humeral bone during a shoulder arthroplasty procedure, it will be understood that the tendon repair systems, devices, components, methods, and instruments described or contemplated herein may be adapted and/or utilized to couple any tendon, ligament, muscle, or other soft tissue to any other tissue or bone in the body.

As will be described in more detail herein, FIGS. 1-16B illustrate various example components that may be utilized in any combination with each other to form any number of different tendon repair systems, or systems for coupling a tendon to a bone. Accordingly, it will be understood that the specific tendon repair systems described herein are non-limiting examples for the purposes of illustration only, and any component(s) described or contemplated herein (or any individual feature(s) of any of the component(s)) may be combined with any other component(s) to form any number of different tendon repair systems.

FIG. 1. illustrates a perspective side view of an example tendon repair system. The tendon repair system may include a bone coupler 10 having a bone-facing surface 11 that may be engageable with a surface 6 of a bone 4 (e.g., a humeral bone, etc.) proximate a bone tunnel 5 formed through the bone 4. The bone coupler 10 may also be referred to herein as a bone coupling device, a bone connection device, or a suture reinforcement device for the bone 4.

The tendon repair system shown in FIG. 1 may also include a flexible element 3 (or a plurality of flexible elements) that may pass through a hole 13 (or a plurality of holes) formed through the bone coupler 10 intermediate and passing through the bone-facing surface 11 and the opposing surface 12 of the bone coupler 10. The flexible element 3 may also be referred to herein as a suture or other stitching material.

In some embodiments, the flexible element 3 may also pass through the bone tunnel 5 (or a plurality of bone tunnels) formed through the bone 4. For example, the second portion 2 of the flexible element 3 may be receivable through the bone tunnel 5 and the hole 13 to engage the opposing surface 12 of the bone coupler 10 and securably couple the tendon 7 to the bone 4. In this manner, the flexible element 3 (or the plurality of flexible elements) may be utilized to couple a tendon 7 (e.g., a subscapularis tendon, etc.) to the bone 4 by tightening and/or tying the flexible elements (or portions of the flexible elements) to bring the tendon 7 and the bone 4 back together to reattach the tendon and promote healing of the bone/tendon interface.

In some embodiments, a first portion 1 of the flexible element 3 may be couplable with the tendon 7 to securably attach the flexible element 3 to the tendon 7 and/or aid in reapproximating the tendon 7 to the bone 4 for reattachment thereto.

In some embodiments, a second portion 2 of the flexible element 3 may be receivable through the bone tunnel 5 and/or the hole 13 formed through the bone coupler 10 to engage an opposing surface 12 of the bone coupler 10 opposite the bone-facing surface 11 and provide a stable platform to securely couple the tendon 7 to the bone 4. For example, the bone coupler 10 may be sufficiently sturdy to prevent the flexible element 3 from migrating and/or ripping through the bone 4 once the flexible element 3 has been tied down and placed under tension.

It will be understood that the bone coupler 10 illustrated in FIG. 1 may be substituted with any other bone coupler embodiment described or contemplated herein (e.g., see FIGS. 12A-16B), or no bone coupler at all.

It will also be understood that any tendon coupler embodiment described or contemplated herein (e.g., see FIGS. 2A and 15A-16B), or no tendon coupler at all, may also be coupled to the tendon 7 by any method disclosed or contemplated herein, as will be discussed in more detail below. It will also be understood that any of the coupled or integrally formed bone coupler and tendon coupler embodiments described or contemplated herein (e.g., see FIGS. 15A-16B) may be coupled to the tendon 7 and/or secured to the bone 4 by any method disclosed or contemplated herein, as will be discussed in more detail.

Figure 2A:
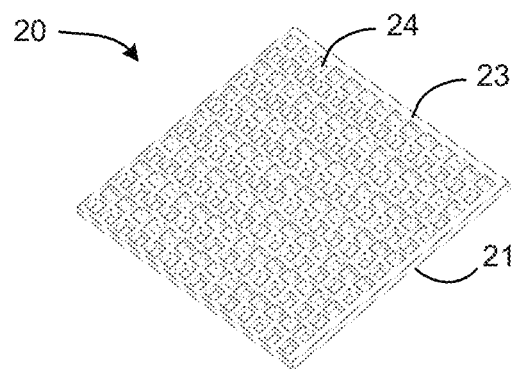
FIG. 2A illustrates a perspective top view of a tendon coupler, according to an embodiment of the present disclosure.
Figure 2B:
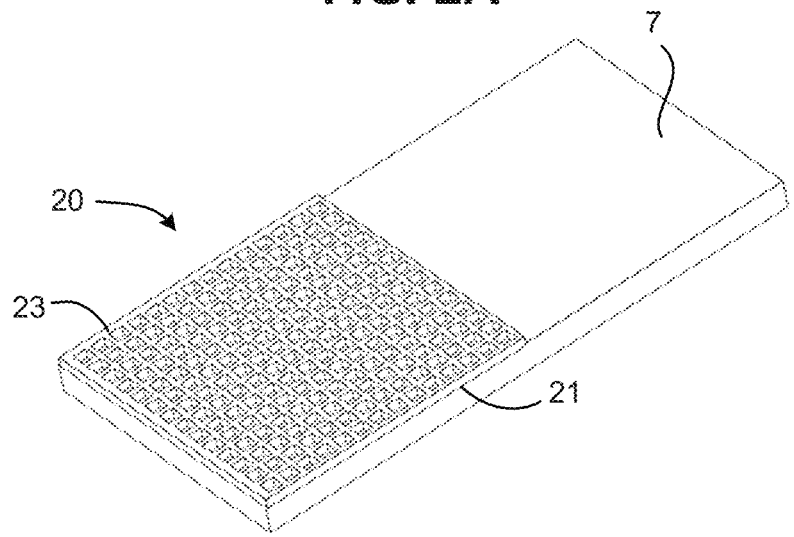
FIG. 2B illustrates a perspective top view of the tendon coupler of FIG. 2A engaged with a tendon.
Figure 2C:
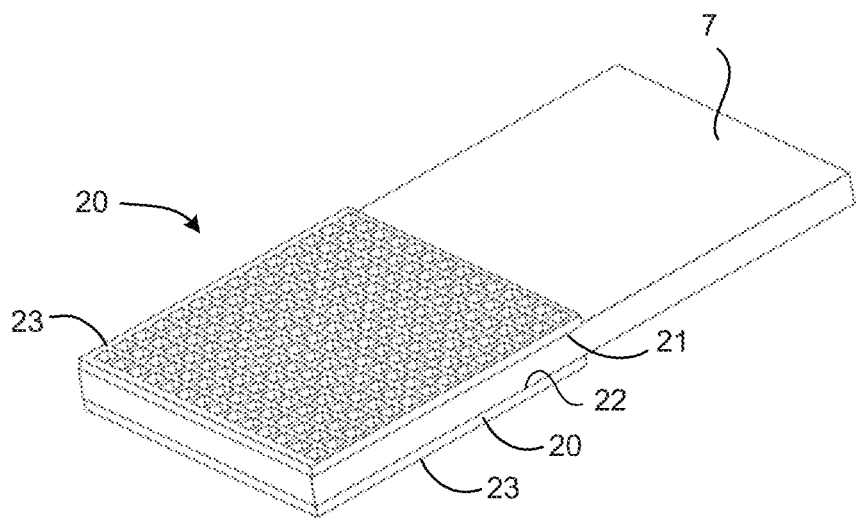
FIG. 2C illustrates a perspective top view of the tendon coupler and tendon of FIG. 2B with a second tendon coupler engaged to the bottom of the tendon.

FIGS. 2A-2C illustrate various views of a tendon coupler 20 for creating a secure connection with a free end of the tendon 7, according to an embodiment of the present disclosure. Specifically, FIG. 2A is a perspective top view of the tendon coupler 20; FIG. 2B shows the tendon coupler 20 engaged with a superior surface of the tendon 7; and FIG. 2C shows a second tendon coupler engaged with an inferior surface of the tendon 7.

The tendon coupler 20 may also be referred to herein as a tendon coupling device, a tendon connection device, or a suture reinforcement device for the tendon.

The tendon coupler embodiments disclosed herein may help prevent suture migration within the tendon 7, enlargement of the suture holes in the tendon 7 due to tension, and/or stretching of the tendon 7.

In some embodiments, the tendon coupler 20 may comprise at least one of: a mesh, a suture mesh, a web, a suture web, a pledget, a pad, a patch, or any other flexible and/or relatively flat structure.

In some embodiments, the tendon coupler 20 may include a tendon-facing surface 21 engageable with the tendon 7 and an outer surface 23.

Figure 16A:
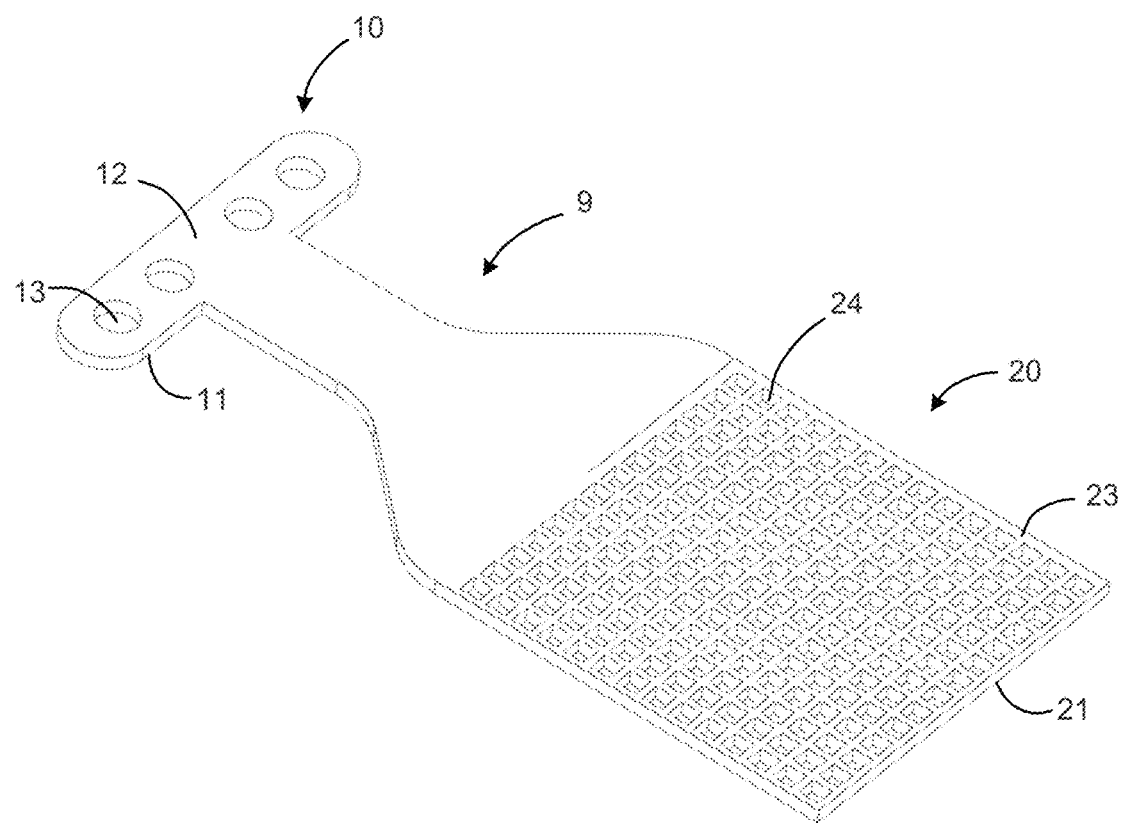
FIG. 16A illustrates a perspective top view of an integrally formed bone coupler and tendon coupler, according to an embodiment of the present disclosure.
Figure 16B:
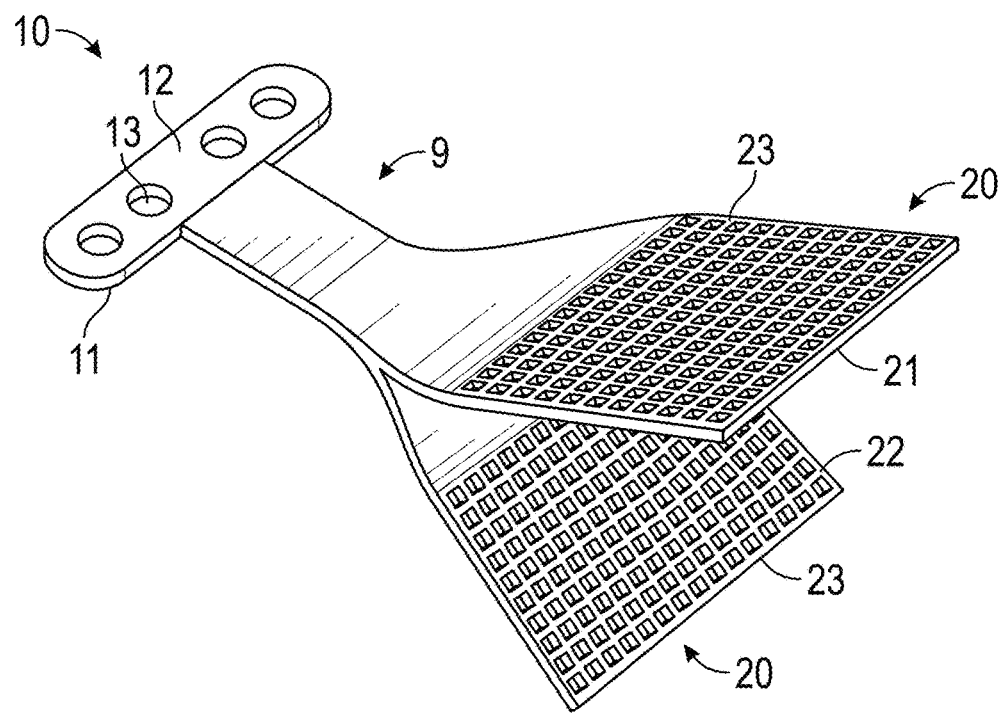
FIG. 16B illustrates a perspective top view of the integrally formed bone coupler and tendon coupler of FIG. 16A with two tendon couplers split apart from each other, according to an embodiment of the present disclosure.

In some embodiments, the tendon-facing surface 21 may comprise a first tendon-facing surface, and the tendon coupler 20 may also include a second tendon-facing surface 22 opposite the first tendon-facing surface (e.g., see FIG. 16B). In these embodiments, the tendon coupler 20 may be split into two separate tendon couplers and the tendon 7 may be inserted between the two tendon couplers and captured therebetween to secure the tendon 7 to the tendon couplers.

In some embodiments, the tendon coupler 20 may be folded around the tendon 7 and the flexible element 3 may penetrate through the tendon coupler 20 and the tendon 7 to secure the tendon 7 to the tendon coupler 20 between opposing sides of the tendon coupler 20.

In some embodiments, the tendon coupler 20 may incorporate one or more biologically active materials (e.g., collagen, growth stimulating proteins, etc.) to promote healing.

In some embodiments, the tendon coupler 20 may be resorbable.

In some embodiments, the tendon coupler 20 may be permanent/not resorbable.

In some embodiments, the tendon coupler 20 may be trimmable such that it can be appropriately sized to a given patient's anatomy.

In some embodiments, the tendon coupler 20 may be secured to the tendon 7 via one or more fasteners.

In some embodiments, the one or more fasteners may include one or more sutures, threads, wires, staples, rivets, other mechanical fasteners, etc.

In some embodiments, the tendon coupler 20 may comprise a mesh design or material that may permit the one or more fasteners to pass through one or more openings 24 formed in the tendon coupler 20.

In some embodiments, the tendon coupler 20 may include one or more sutures extending from the tendon coupler 20 that may be utilized to secure the tendon/tendon coupler construct back to the bone 4.

In some embodiments, a first tendon coupler may be placed on a first side of the tendon 7 (e.g., see FIG. 2B), and/or a second tendon coupler may be placed on a second or opposing side of the tendon 7 (e.g., see FIG. 2C).

In some embodiments, the two tendon couplers may have opposing mating features that may lock together when the tendon couplers are compressed against the tendon 7. These mating features may pass through the tendon 7 to lock the tendon couplers on each side of the tendon 7 and may be hollow to allow the suture to pass through the mating features, as will be discussed below in more detail.

Figure 3A:
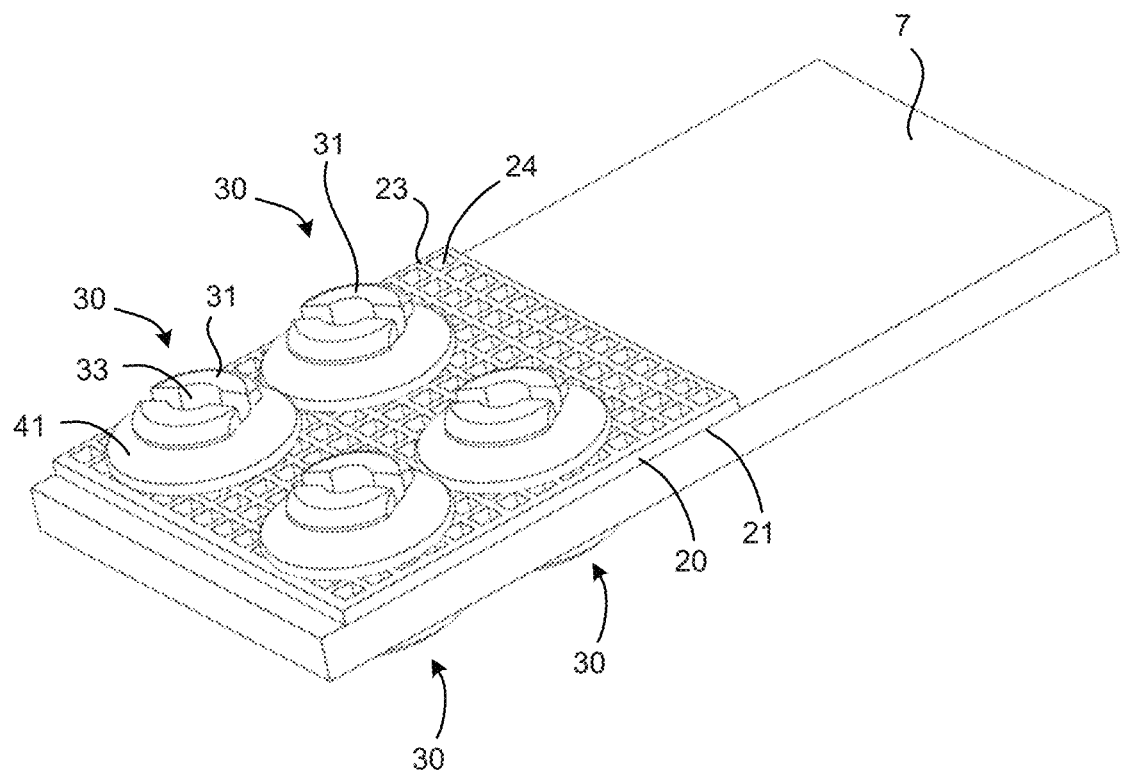
FIG. 3A illustrates a perspective top view of the tendon coupler and tendon shown in FIG. 2B with a plurality of fasteners coupled therethrough, according to an embodiment of the present disclosure.
Figure 3B:
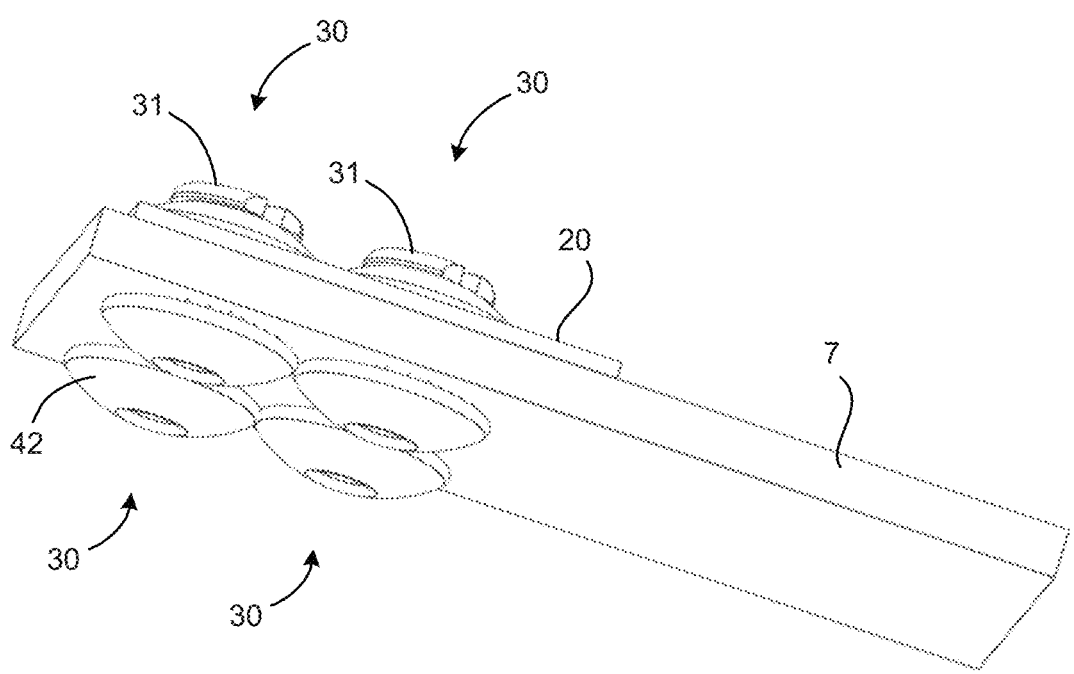
FIG. 3B illustrates a perspective bottom view of the tendon coupler, tendon, and fasteners shown in FIG. 3A.
Figure 4A:
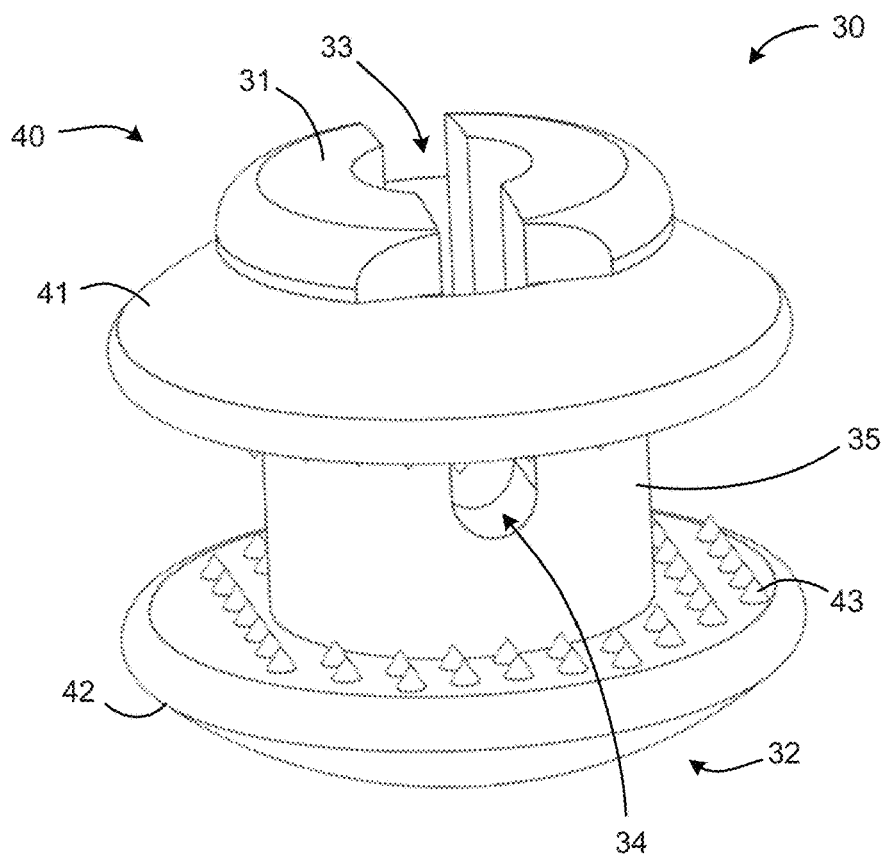
FIG. 4A illustrates a perspective top view of one of the fasteners of FIG. 3A.
Figure 4B:
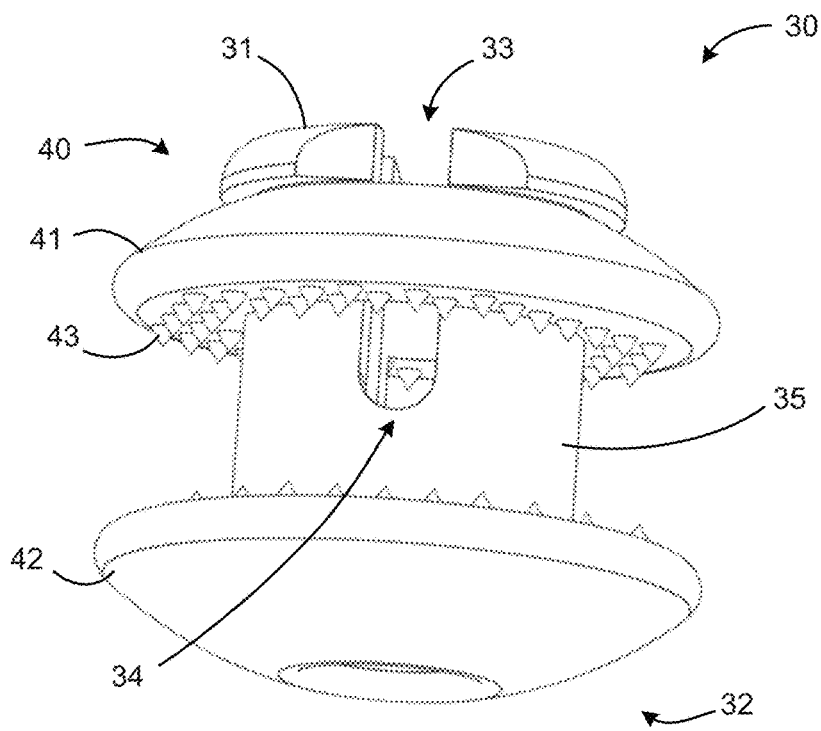
FIG. 4B illustrates a perspective bottom view of the fastener shown in FIG. 4A.
Figure 5:
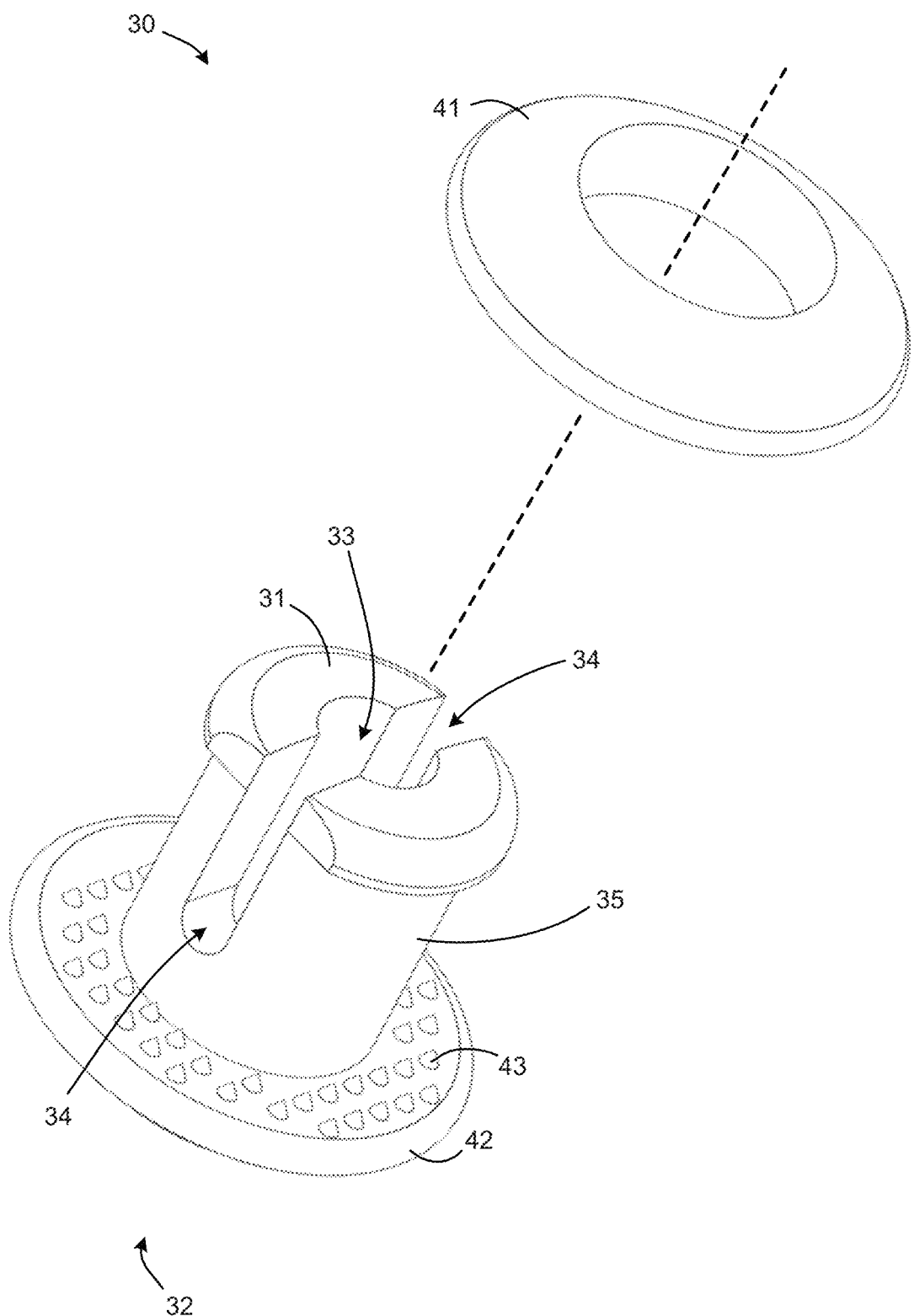
FIG. 5 illustrates an exploded view of the fastener shown in FIG. 4A.

FIGS. 3A-5 illustrate various views of a fastener 30 or system of fasteners for coupling the various tendon coupler embodiments disclosed herein to the tendon 7. Specifically, FIG. 3A is a perspective top view of the tendon coupler 20 and tendon 7 of FIG. 2B with a plurality of fasteners coupled therethrough; FIG. 3B is a perspective bottom view of FIG. 3A; FIG. 4A is a perspective top view of one of the fasteners from FIG. 3A; FIG. 4B is a perspective bottom view of the fastener 30 shown in FIG. 4A; and FIG. 5 is an exploded view of the fastener 30 shown in FIGS. 4A and 4B. The fastener 30 may also be referred to herein as a first fastener, a second fastener, etc.

In some embodiments, the fastener 30 may comprise a mechanical fastener configured to secure the tendon 7 to the tendon coupler 20.

In some embodiments, the first portion 1 of the flexible element 3 may be couplable with the fastener 30 to securably attach the flexible element 3 to the tendon 7.

In some embodiments, the fastener 30 may include a fastener shaft 35 having a first end 31, a second end 32, and a longitudinal passageway 33 formed through the fastener shaft 35 intermediate the first end 31 and the second end 32.

In some embodiments, the fastener 30 may also include a first button 41 coupled to the first end 31 of the fastener shaft 35, and a second button 42 coupled to the second end 32 of the fastener shaft 35.

In some embodiments, the first button 41 and/or the second button 42 may include one or more retention features 43 (e.g., spikes, roughened surface, etc.) to help grasp and hold the tendon coupler 20 and/or the tendon 7.

In some embodiments, the fastener shaft 35 may be configured to penetrate through the tendon 7 and the tendon coupler 20 to secure the tendon coupler 20 to the tendon 7 intermediate the first button 41 and the second button 42.

In some embodiments, the first portion 1 of the flexible element 3 may be receivable through the longitudinal passageway 33 of the fastener shaft 35 to securably attach the flexible element 3 to the tendon 7.

In some embodiments, the fastener 30 may include a locking mechanism 40 formed intermediate the fastener shaft 35 and at least one of the first button 41 and the second button 42.

In some embodiments, the locking mechanism 40 may be configured to couplably secure the fastener shaft 35 to at least one of the first button 41 and the second button 42.

In some embodiments, the locking mechanism 40 may comprise a one-way or unidirectional locking mechanism that allows for movement in one direction but resists motion in the opposing direction.

In some embodiments, the locking mechanism 40 may comprise one or more collet slots 34 formed in the fastener shaft 35. The one or more collet slots 34 may be configured to deform inwardly to allow one of the first button 41 and the second button 42 to connect to the fastener shaft 35 in a first direction, and then deform outwardly to resist removal of the first button 41 or the second button 42 in a second direction after the first button 41 or the second button 42 has been connected to the fastener shaft 35. In this manner, the fastener shaft 35 may pass through or penetrate the tendon coupler 20 and the tendon 7 and then one of the first button 41 and the second button 42 may be locked to the fastener shaft 35 to trap the tendon/tendon coupler construct between the first button 41 and the second button 42. Moreover, the flexible element 3, or the first portion 1 of the flexible element 3, may then be passed through the longitudinal passageway 33 of the fastener shaft 35 to securably attach the flexible element 3 to the tendon/tendon coupler construct and enable reattachment of the tendon 7 to the bone 4.

In some embodiments, any of the fasteners or system of fasteners described or contemplated herein may comprise at least one of: a bone staple, a bone screw, a bone anchor, one or more sutures, threads, wires, rivets, other mechanical fasteners, the flexible element 3, the first portion 1 of the flexible element 3, the second portion 2 of the flexible element 3, etc.

Figure 6A:
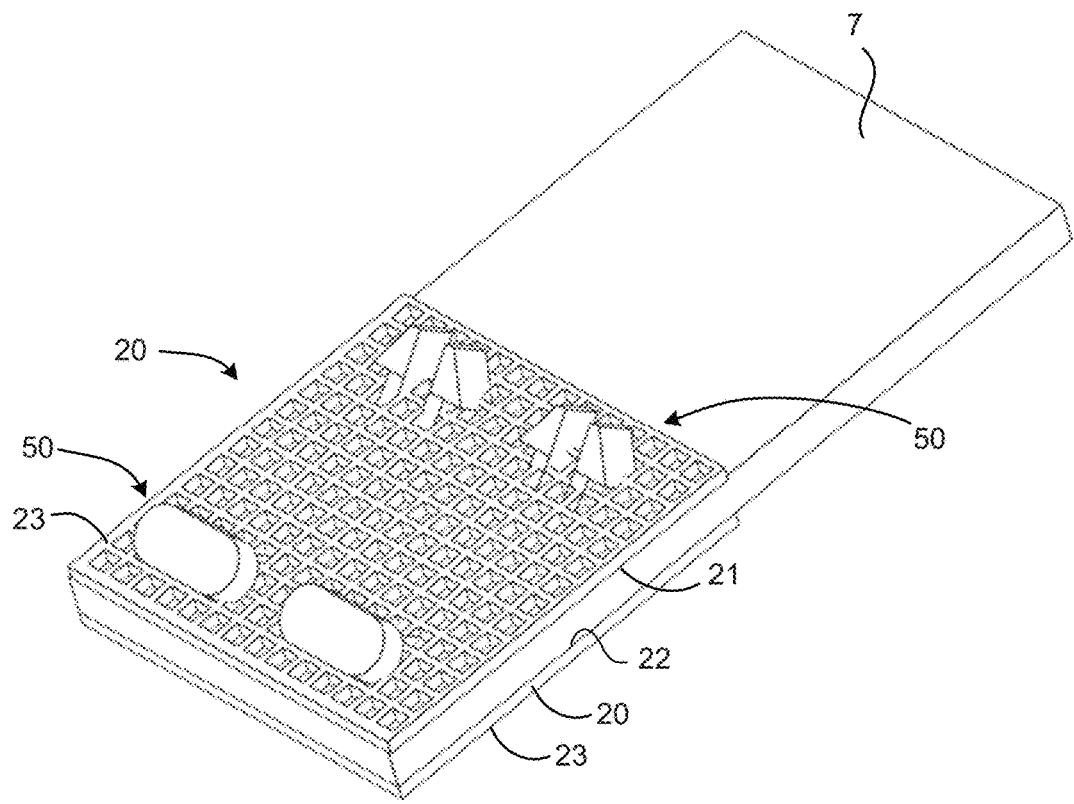
FIG. 6A illustrates a perspective top view of the tendon couplers and tendon shown in FIG. 2C with a plurality of curved fasteners coupled therethrough, according to an embodiment of the present disclosure.
Figure 6B:
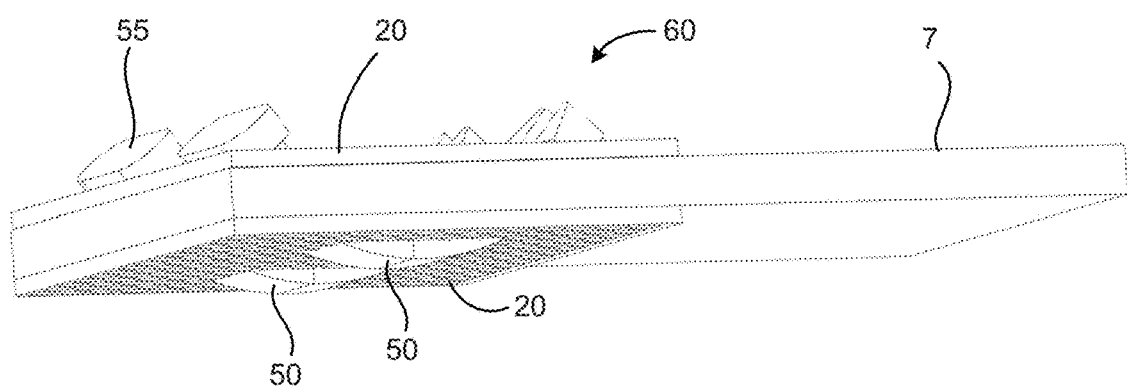
FIG. 6B illustrates a perspective side view of the tendon couplers, tendon, and curved fasteners shown in FIG. 6A.
Figure 7A:
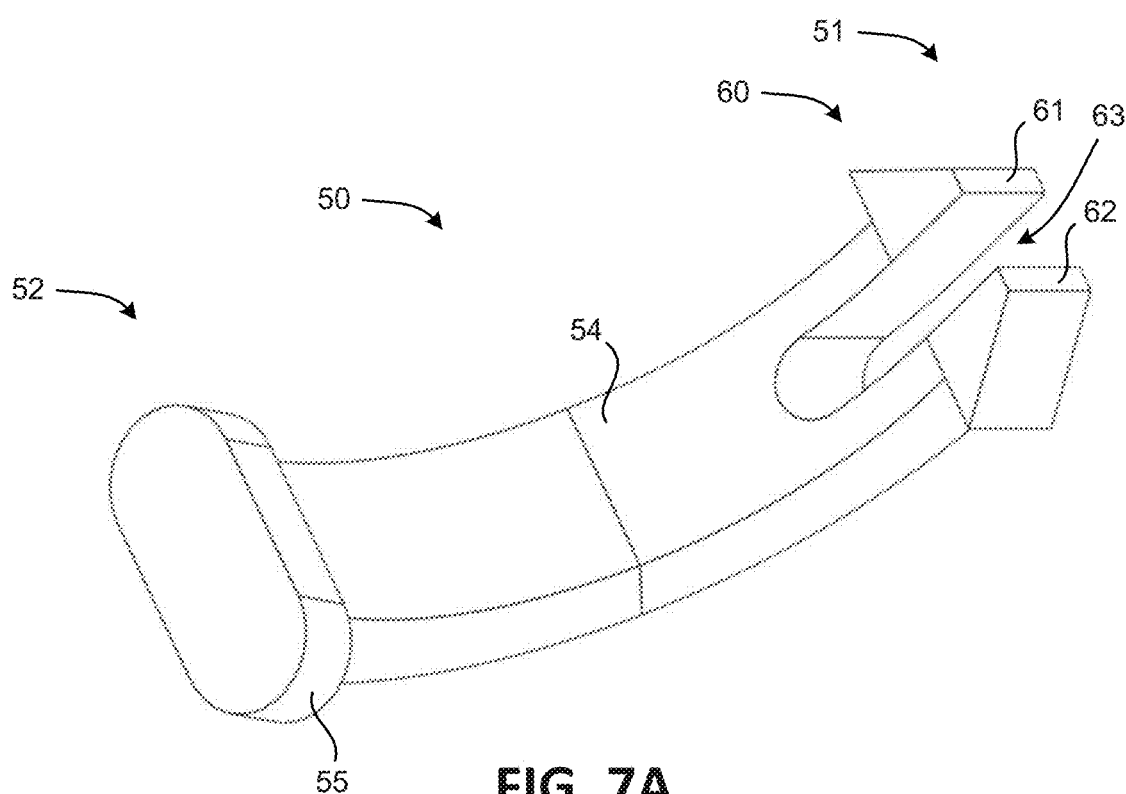
FIG. 7A illustrates a perspective top view of one of the curved fasteners of FIG. 6A.
Figure 7B:
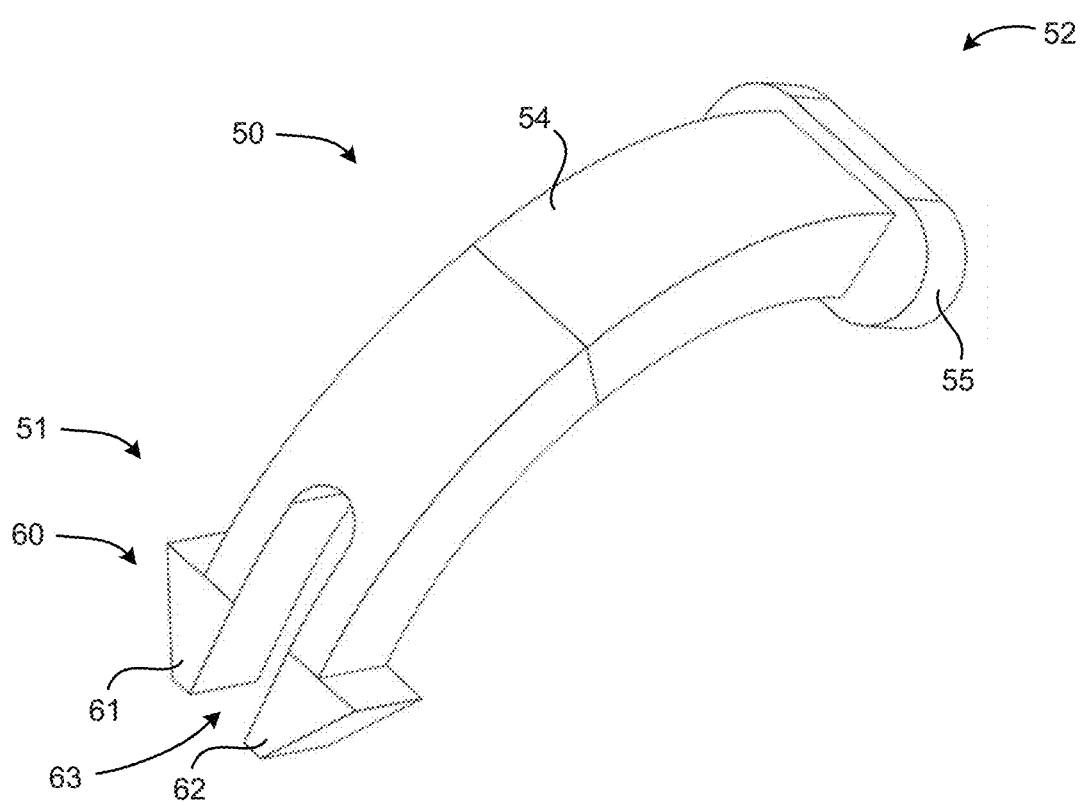
FIG. 7B illustrates a perspective bottom view of the curved fastener shown in FIG. 7A.
Figure 7C:
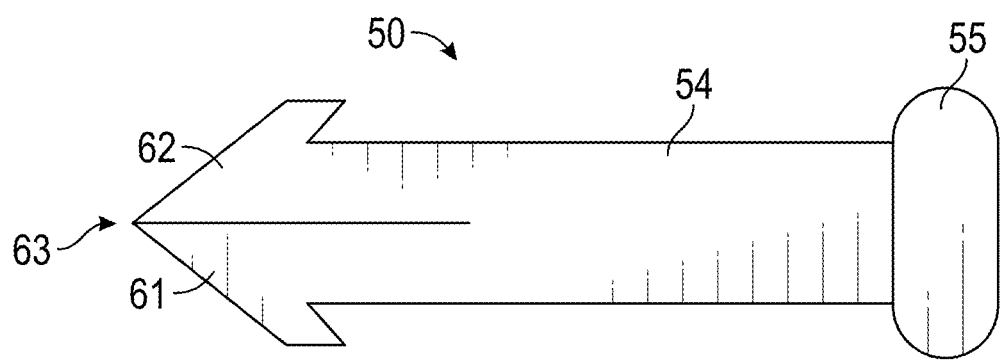
FIG. 7C illustrates a top view of the curved fastener of FIG. 7A in a compressed state.
Figure 7D:
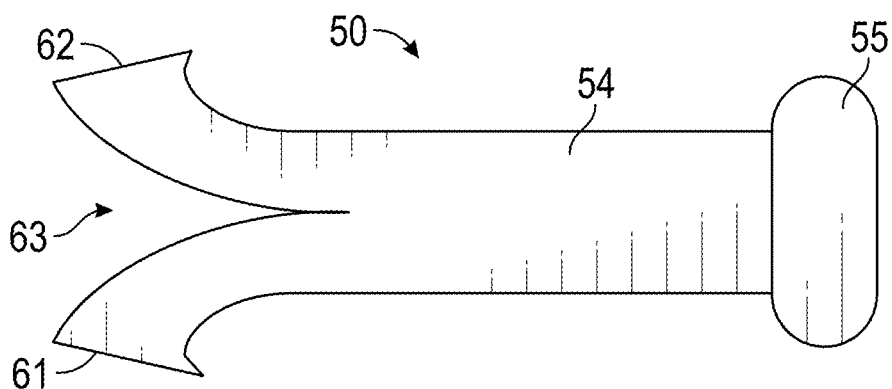
FIG. 7D illustrates a top view of the curved fastener of FIG. 7A in an expanded state.
Figure 8:
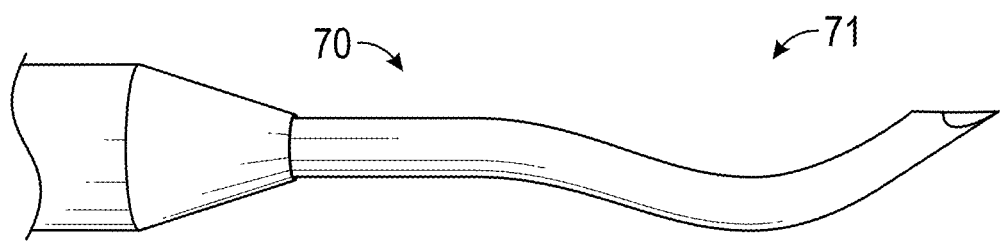
FIG. 8 illustrates a side view of a curved fastener inserter tool, according to an embodiment of the present disclosure.

FIGS. 6A-8 illustrate various views of a curved fastener 50 or system of curved fasteners for coupling the various tendon coupler embodiments disclosed herein to the tendon 7. Specifically, FIG. 6A is a perspective top view of the tendon couplers and tendon shown in FIG. 2C with a plurality of curved fasteners coupled therethrough; FIG. 6B is a perspective side view of FIG. 6A; FIG. 7A is a perspective top view of one of the curved fasteners shown in FIG. 6A; FIG. 7B is a perspective bottom view of the curved fastener 50 shown in FIG. 7A; FIG. 7C is a top view of the curved fastener 50 in a compressed state; FIG. 7D is a top view of the curved fastener 50 in an expanded state; and FIG. 8 is a side view of a curved fastener inserter tool 70 with a curved tip 71 that may be utilized to insert the curved fastener 50 into a tendon/tendon coupler construct. The curved fastener 50 may also be referred to herein as a first fastener, a second fastener, etc.

In some embodiments, the curved fastener 50 may be configured to secure the tendon 7 to the tendon coupler 20, or a plurality of tendon couplers.

In some embodiments, the first portion 1 of the flexible element 3 may be couplable with the curved fastener 50 to securably attach the flexible element 3 to the tendon 7.

In some embodiments, the curved fastener 50 may include a curved fastener shaft 54 having a leading end 51, a trailing end 52, a barbed feature 60 coupled to the leading end 51, and a stop feature 55 coupled to the trailing end 52.

In some embodiments, the barbed feature 60 may be configured to penetrate through the tendon 7 and the tendon coupler 20 (or tendon couplers) to secure the tendon coupler 20 to the tendon 7 intermediate the barbed feature 60 and the stop feature 55.

In some embodiments, the first portion 1 of the flexible element 3 may be couplable with the curved fastener 50 to securably attach the flexible element 3 to the tendon 7.

In some embodiments, the barbed feature 60 may include a first barbed end 61, a second barbed end 62, and a gap 63 formed intermediate the first barbed end 61 and the second barbed end 62.

In a first compressed state, the first barbed end 61 and the second barbed end 62 may be compressed toward each other (e.g., see FIG. 7C). In this configuration, the leading end 51 of the curved fastener 50 may be insertable through the tendon/tendon coupler construct. The curved fastener inserter tool 70 shown in FIG. 8 may be utilized to insert the curved fastener 50 through the tendon/tendon coupler construct in the compressed state with the curved fastener 50 held inside the curved tip 71 of the curved fastener inserter tool 70. Once the curved fastener 50 is in place, it may be ejected from the curved fastener inserter tool 70 and assume a second expanded state. In the second expanded state, the first barbed end 61 and the second barbed end 62 may expand away from each other (e.g., see FIG. 7D) to prevent the curved fastener 50 from backing out of the tendon/tendon coupler construct.

In some embodiments, the first portion 1 of the flexible element 3 may be couplable with the curved fastener 50 to securably attach the flexible element 3 to the tendon 7. For example, the flexible element 3 may be couplable with the gap 63, the barbed feature 60, the stop feature 55, etc.

In some embodiments, any of the fasteners or system of fasteners described or contemplated herein may comprise at least one of: a bone staple, a bone screw, a bone anchor, one or more sutures, threads, wires, rivets, other mechanical fasteners, the flexible element 3, the first portion 1 of the flexible element 3, the second portion 2 of the flexible element 3, etc.

Figure 9:
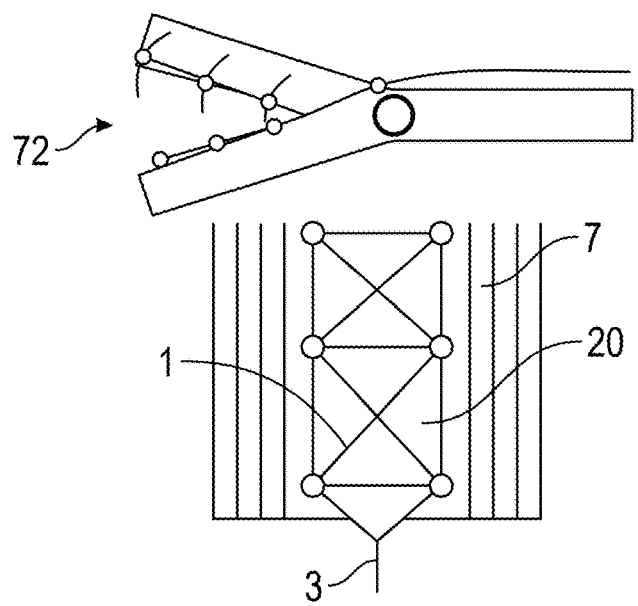
FIG. 9 illustrates a tendon coupler secured to a tendon with a suture web and a tendon coupler attachment tool, according to an embodiment of the present disclosure.
Figure 10:
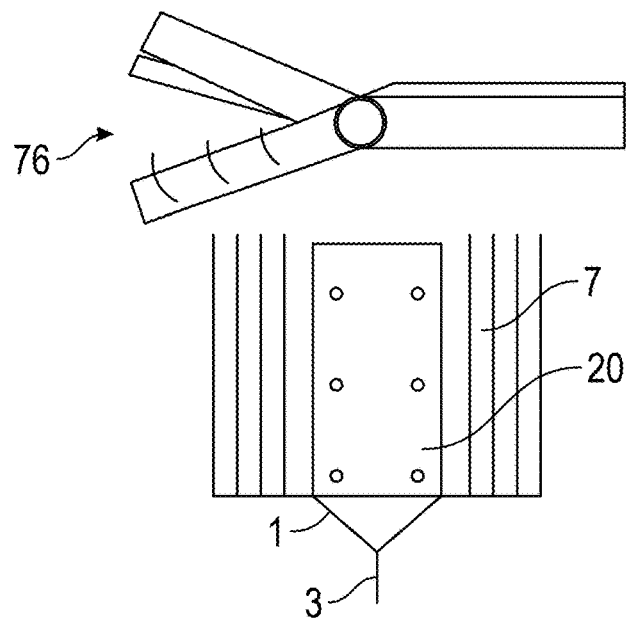
FIG. 10 illustrates a tendon coupler secured to a tendon and a tendon coupler attachment tool, according to another embodiment of the present disclosure.

FIGS. 9 and 10 illustrate instruments that may couple the tendon coupler 20 to the tendon 7, according to embodiments of the present disclosure. Specifically, FIG. 9 illustrates a first tendon coupler attachment tool 72 that may be utilized to secure the tendon coupler 20 to The tendon 7 with the flexible element 3 (or the first portion 1 of the flexible element 3) via a suture web, and FIG. 10 illustrates a second tendon coupler attachment tool 76 that may be utilized to secure the tendon coupler 20 to the tendon 7 with the flexible element 3 (or the first portion 1 of the flexible element 3) via one or more sutures placed therethrough, according to another embodiment of the present disclosure.

In this manner, the tendon coupler 20 may be temporarily affixed to these inserter devices, and these inserter devices may then enable the tendon coupler 20 to be placed onto the tendon 7 and secured thereto as the inserter device is actuated.

Figure 11:
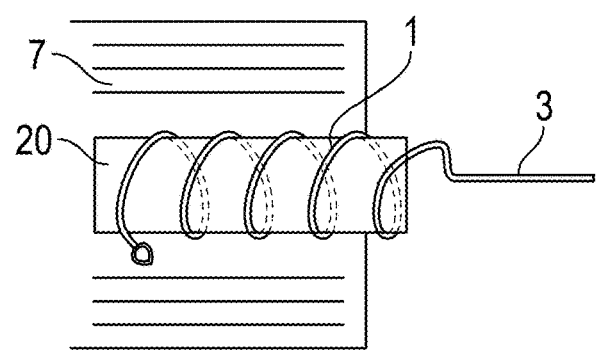
FIG. 11 illustrates a tendon coupler secured to a tendon with a suture weaved around the tendon coupler and the tendon, according to an embodiment of the present disclosure.

FIG. 11 illustrates the tendon coupler 20 secured to the tendon 7 with the flexible element 3 (or the first portion 1 of the flexible element 3) that may be weaved around the tendon/tendon coupler construct to secure the tendon coupler 20 to the tendon 7, according to another embodiment of the present disclosure.

Figure 12A:
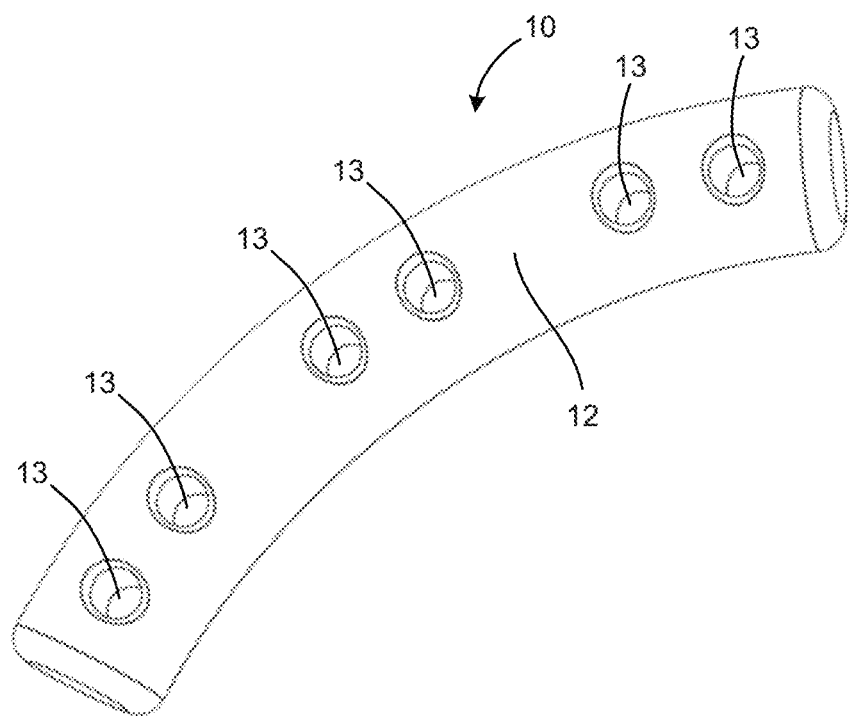
FIG. 12A illustrates a perspective top view of a bone coupler, according to an embodiment of the present disclosure.
Figure 12B:
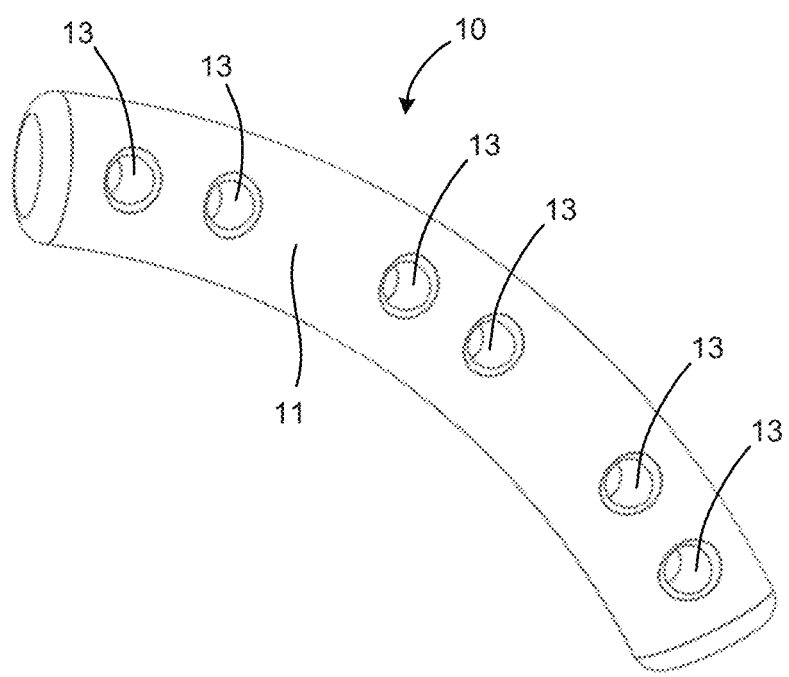
FIG. 12B illustrates a perspective bottom view of the bone coupler of FIG. 12A.
Figure 13A:
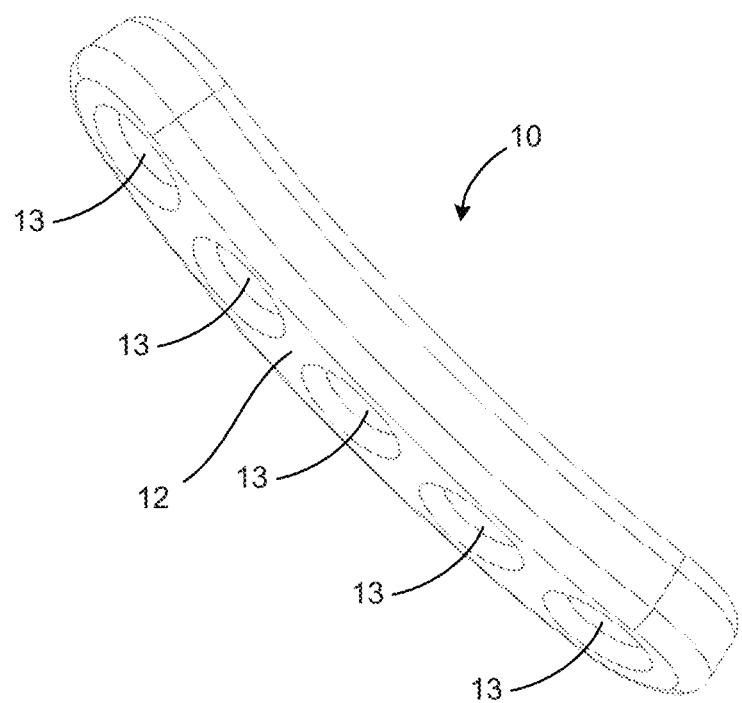
FIG. 13A illustrates a perspective top view of a bone coupler, according to an embodiment of the present disclosure.
Figure 13B:
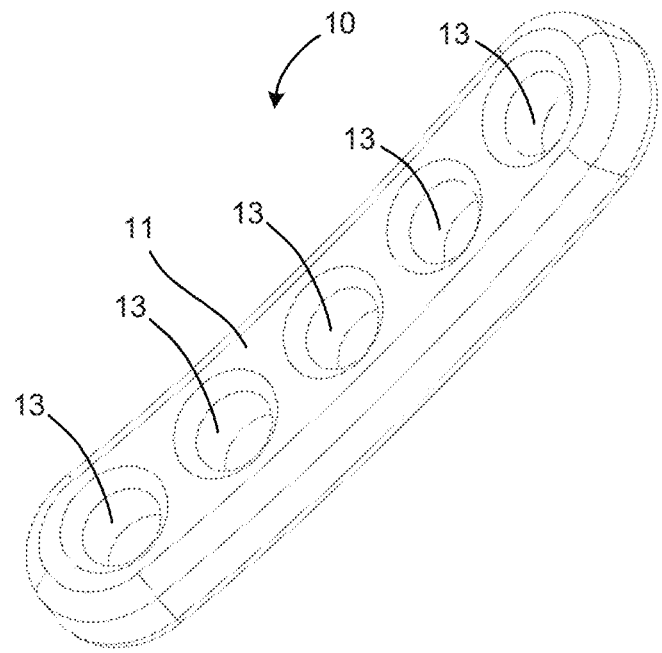
FIG. 13B illustrates a perspective bottom view of the bone coupler of FIG. 13A.

FIGS. 12A-14B illustrate various views of bone coupler embodiments of the present disclosure. Specifically, FIGS. 12A and 12B are perspective top and bottom views of a first bone coupler embodiment; FIGS. 13A and 13B are perspective top and bottom views of a second bone coupler embodiment; and FIGS. 15A and 15B are perspective top and bottom views of a third bone coupler embodiment.

As previously discussed, each of the different embodiments of the bone coupler 10 may include the bone-facing surface 11, the opposing surface 12, and the hole 13 (or a plurality of holes) formed through the bone coupler 10 intermediate and passing through the bone-facing surface 11 and the opposing surface 12.

The bone coupler 10 may provide a structure that the suture can be tensioned/tightened against as the tendon 7 is secured into position against the bone 4. In this manner, the bone coupler 10 may prevent the suture from cutting through the bone 4.

In some embodiments, the bone coupler 10 may comprise a rigid column or barrel structure.

In some embodiments, the bone coupler 10 may comprise at least one of: a straight shape, a curved shape, a cylindrical shape, a flat shape, a rectangular shape, a round shape, an oval shape, a plate-like shape, etc.

In some embodiments, the bone coupler 10 may be sized and shaped to fit within a bicipital groove of a humeral bone proximate one or more bone tunnels that may be formed in/near the bicipital groove.

In some embodiments, the hole 13 or plurality of holes may be configured to receive the flexible element 3, suture, or other fastening materials therethrough.

In some embodiments, the bone coupler 10 may also include grooves, channels, and/or indentations (not shown) formed in/on the bone coupler 10 to receive the fastening materials therein.

In some embodiments, a tensioning instrument (not shown) may be supplied with and/or incorporated into the bone coupler 10 to enable the suture to be pulled tight and/or tensioned appropriately to accomplish the tendon repair procedure.

In some embodiments, the bone coupler 10 (or any other component described or contemplated herein) may comprise any material including, but not limited to: plastics, metals, textiles, PEEK, hydroxyapatite, etc., or combinations thereof.

In some embodiments, the bone coupler 10 may be made of plastic with metallic eyelets or reinforcement regions (not shown) to help prevent the suture from cutting through or breaking the bone coupler 10.

In some embodiments, suture material may be pre-loaded within/on the bone coupler 10 to provide greater ease of use.

In some embodiments, the bone coupler 10 may have spikes and/or other projections (not shown) on a surface of the bone coupler 10 that may aid in securing the bone coupler 10 against the bone 4 (or soft tissues) to prevent the bone coupler 10 from sliding or moving relative to the bone 4 (or soft tissues) after implantation.

In some embodiments, the bone coupler 10 may be configured to be preloaded into an instrument for ease of use.

In some embodiments, the bone coupler 10 may be flexible to conform to various different anatomical features. In these embodiments, the bone coupler 10 (or any other component described or contemplated herein) may be manufactured from a flexible material including, but not limited to: polytetrafluoroethylene, polypropylene, polyester, polyurethane, nylon, other synthetic or non-synthetic materials, etc., or combinations thereof.

In some embodiments, the bone coupler 10 may have a relatively flat shape, with the ability to pass a suture through it using a needle and/or other suture passing device.

In some embodiments, the bone coupler 10 may be pierceable with a needle or other object to pass a suture therethrough. In these embodiments, the bone coupler 10 may have an adequate thickness that is strong enough to prevent the suture from ripping through the walls of the bone coupler 10.

In some embodiments, the bone coupler 10 may include suture strands that are manufactured as part of the bone coupler 10 (or that may come pre-loaded within the bone coupler 10) to improve the fixation strength of the suture/bone coupler construct.

FIGS. 15A-16B illustrate various views of two combined bone coupler and tendon coupler constructs, according to embodiments of the present disclosure. Specifically, FIGS. 15A and 15B are perspective views of a first combined bone coupler and tendon coupler construct, and FIGS. 16A and 16B are perspective views of a second integrally formed bone coupler and tendon coupler construct.

Figure 14A:
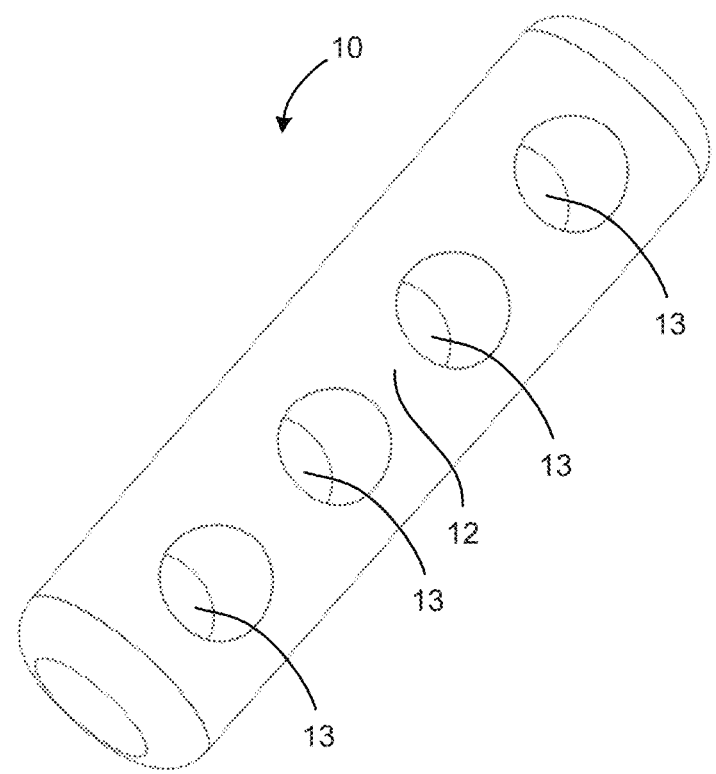
FIG. 14A illustrates a perspective top view of a bone coupler, according to another embodiment of the present disclosure.
Figure 14B:
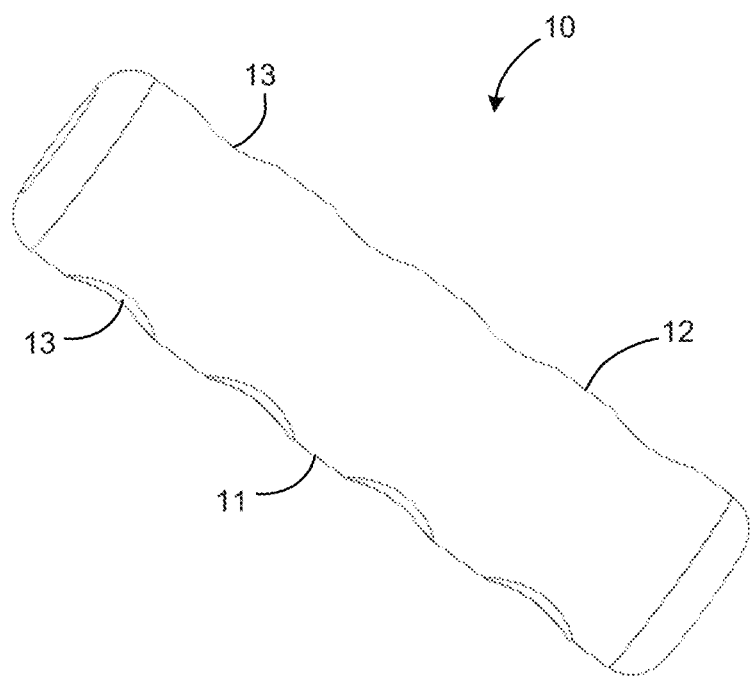
FIG. 14B illustrates a perspective side view of the bone coupler of FIG. 14A.
Figure 15A:
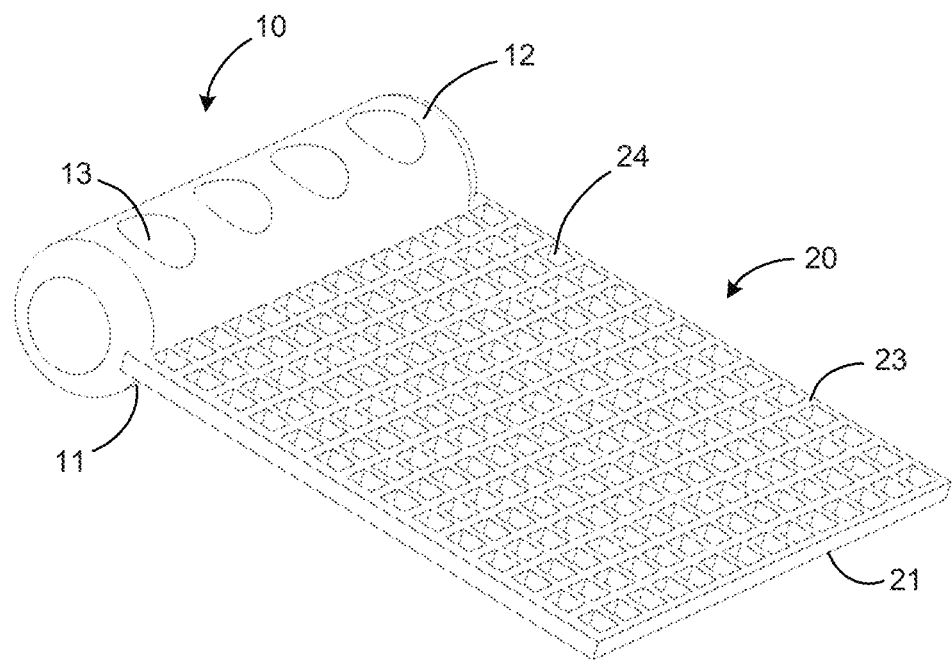
FIG. 15A illustrates a perspective top view of the bone coupler of FIG. 14 coupled to the tendon coupler of FIG. 2A, according to an embodiment of the present disclosure.
Figure 15B:
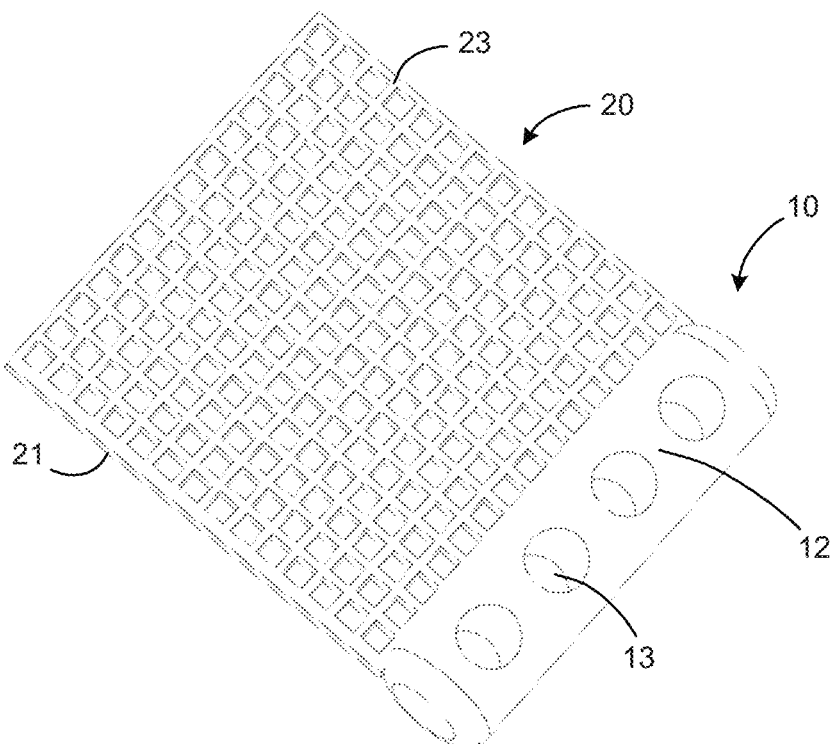
FIG. 15B illustrates another perspective top view of the bone coupler and tendon coupler construct shown in FIG. 15A.

In some embodiments, the bone coupler 10 shown in FIGS. 14A and 14B may be directly coupled/connected to the tendon coupler 20 of FIG. 2A to create the combined bone and tendon coupler construct shown in FIGS. 15A and 15B.

In some embodiments, a first fastener may be configured to couple the tendon coupler 20 to the tendon 7, and a second fastener may be configured to secure the bone coupler 10 to the surface 6 of the bone 4 to securely couple the tendon 7 to the bone 4.

In some embodiments, any of the fasteners or system of fasteners described or contemplated herein may comprise at least one of: a bone staple, a bone screw, a bone anchor, one or more sutures, threads, wires, rivets, other mechanical fasteners, the flexible element 3, the first portion 1 of the flexible element 3, the second portion 2 of the flexible element 3, etc.

In some embodiments, the tendon coupler 20 of FIG. 2A may be integrally formed with the bone coupler 10, as shown in FIGS. 16A and 16B.

In some embodiments, an intermediate portion 9 may couple the tendon coupler 20 to the bone coupler 10.

In some embodiments, the bone coupler 10 may comprise a flexible material that may conform to an anatomical feature of a patient, such as a surface of a bone.

In some embodiments, the tendon coupler 20 may be split into two separate tendon couplers such that the tendon 7 may be inserted between the two tendon couplers and captured therebetween to secure the tendon 7 to the tendon couplers (e.g., see FIG. 16B). In these embodiments, the tendon-facing surface 21 may comprise a first tendon-facing surface, and the construct may also include a second tendon-facing surface 22 opposite the first tendon-facing surface.

Figure 17:
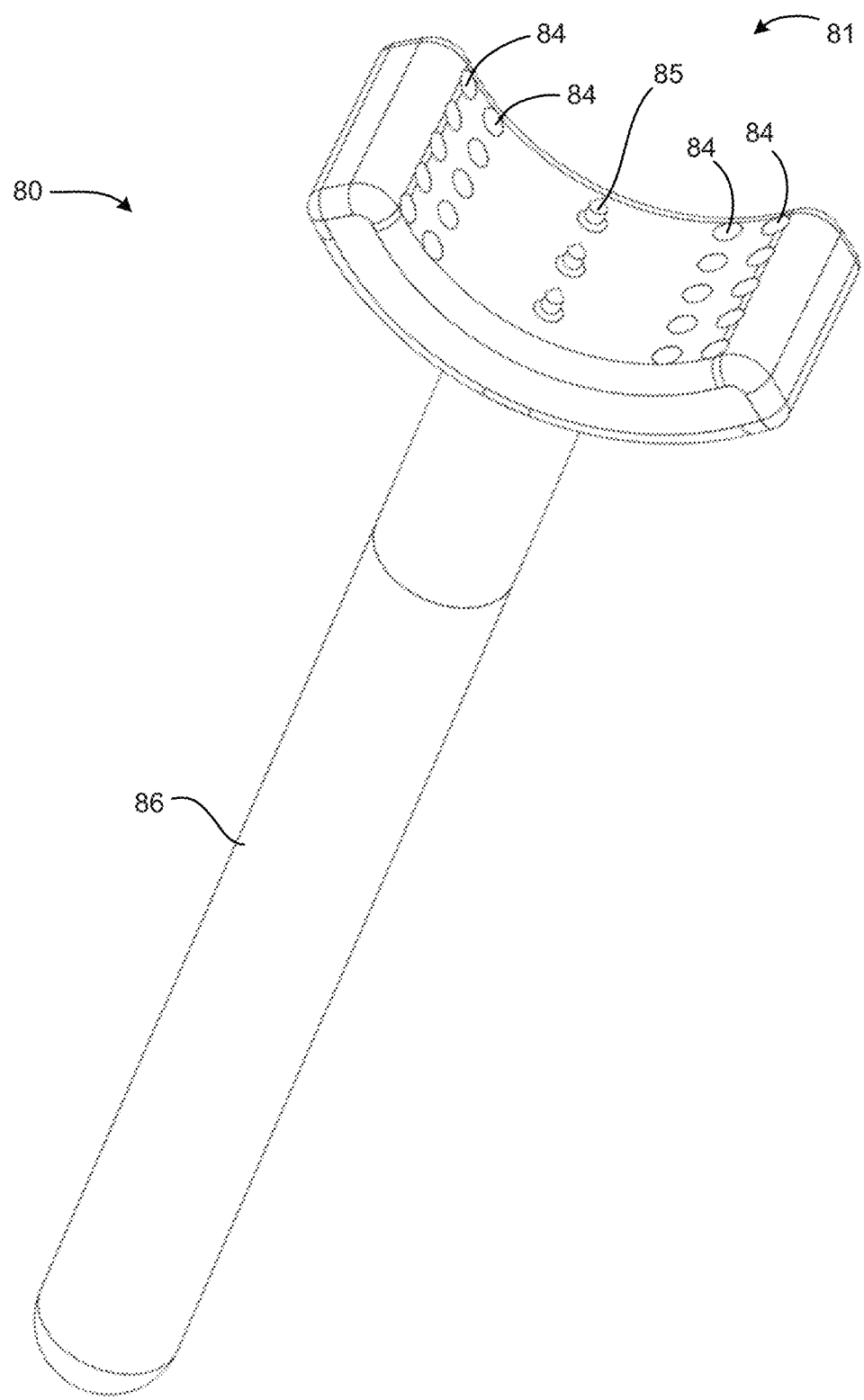
FIG. 17 illustrates a perspective view of a drill guide, according to an embodiment of the present disclosure.
Figure 18:
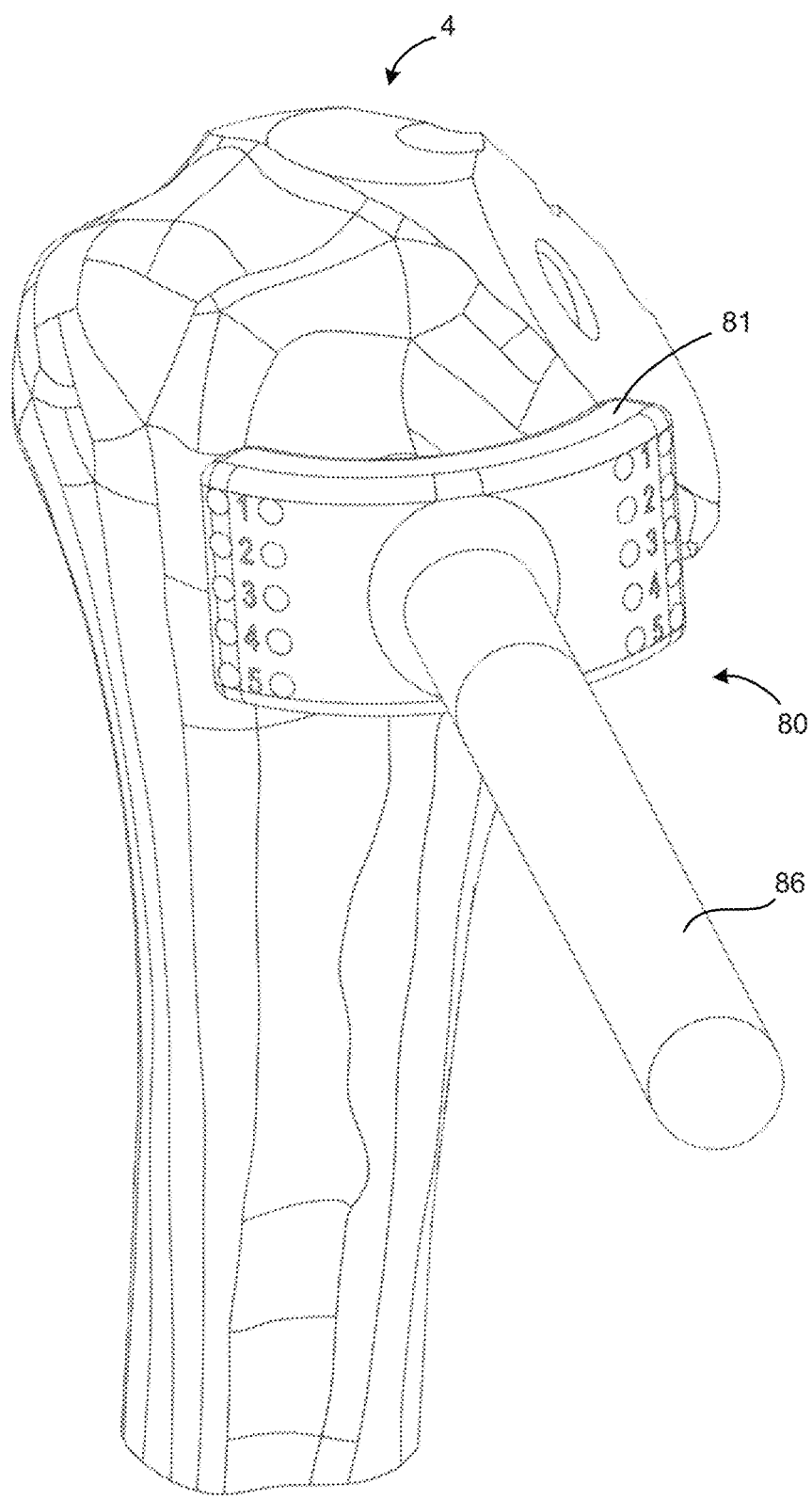
FIG. 18 illustrates a perspective view of the drill guide of FIG. 17 engaged with a bone.
Figure 19:
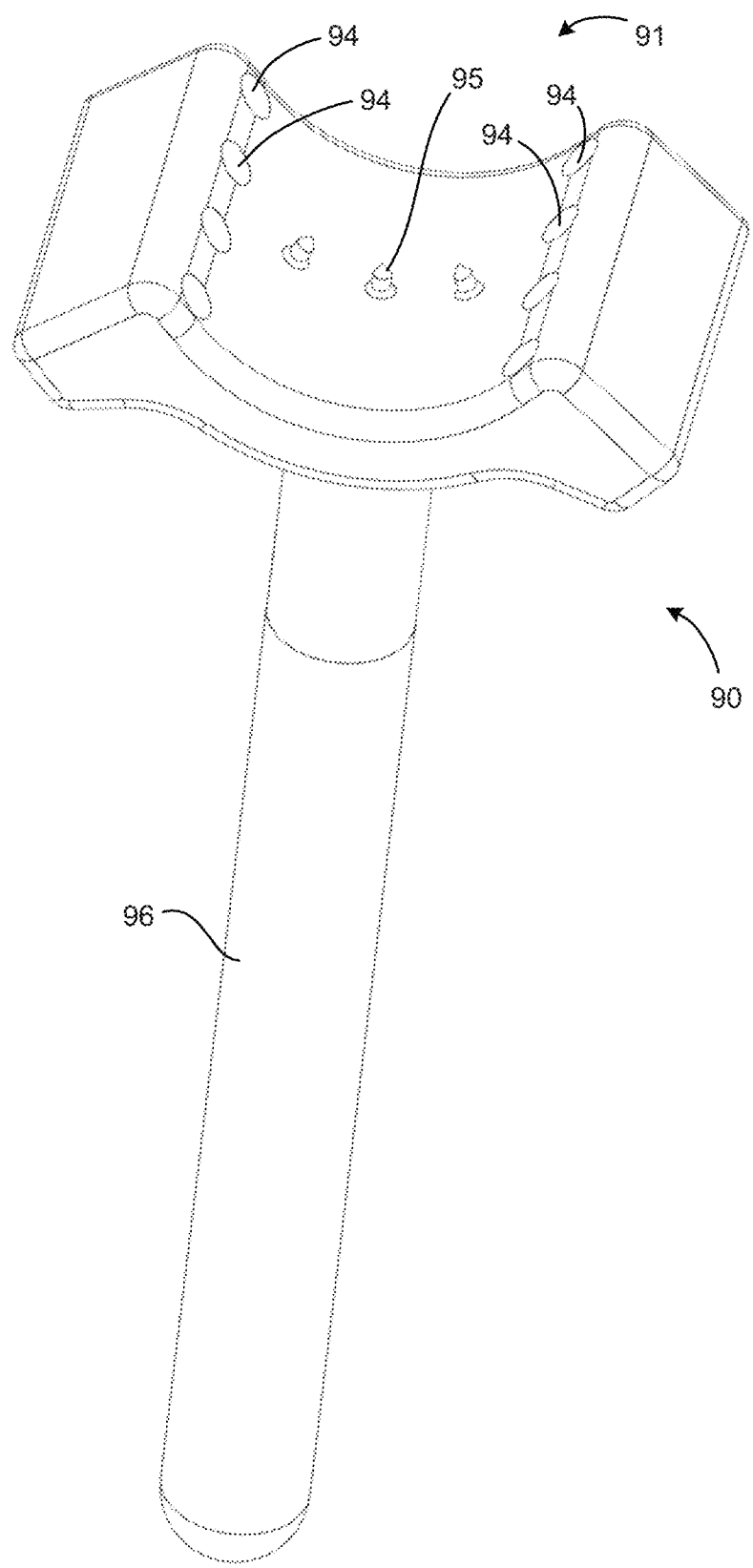
FIG. 19 illustrates a perspective view of a drill guide, according to another embodiment of the present disclosure.
Figure 20:
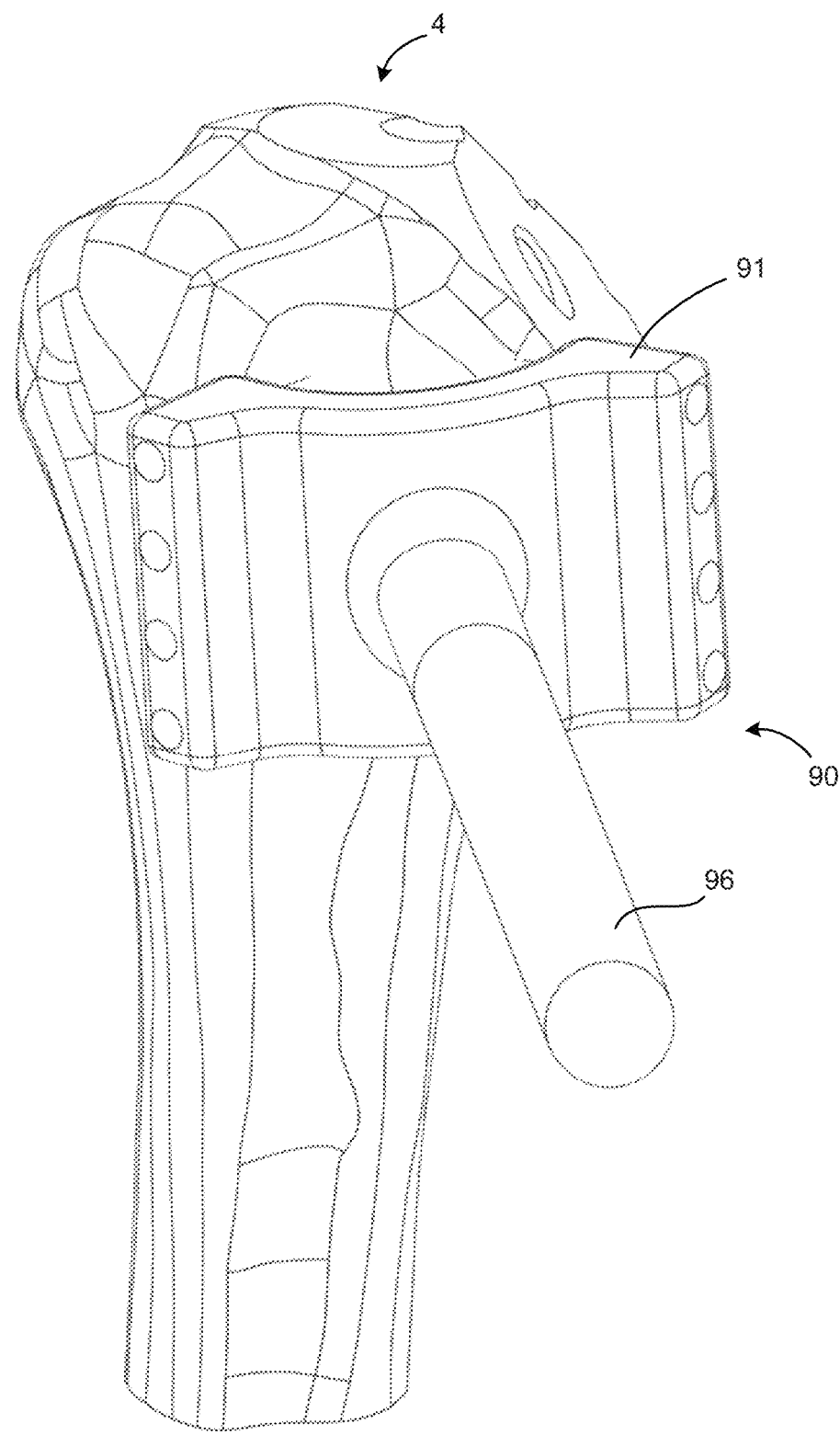
FIG. 20 illustrates a perspective view of the drill guide of FIG. 19 engaged with a bone.
Figure 21:
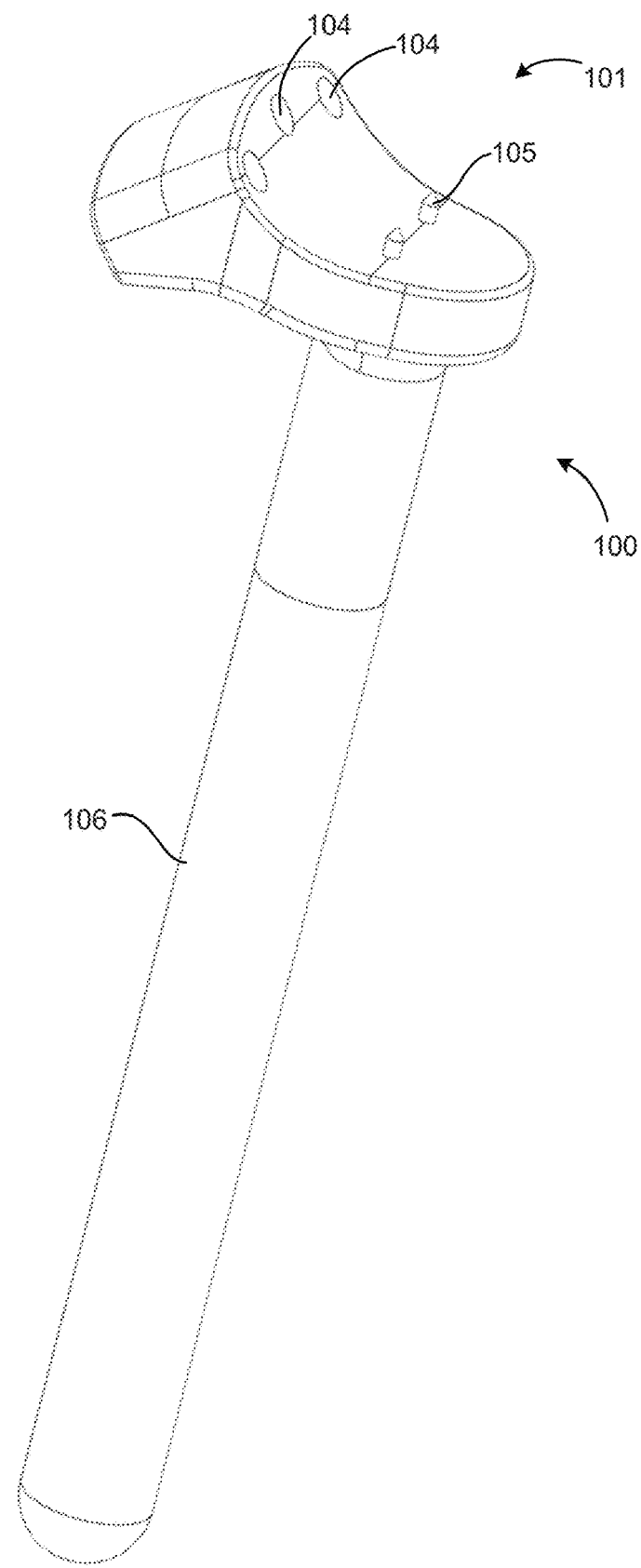
FIG. 21 illustrates a perspective view of a drill guide, according to another embodiment of the present disclosure.
Figure 22:
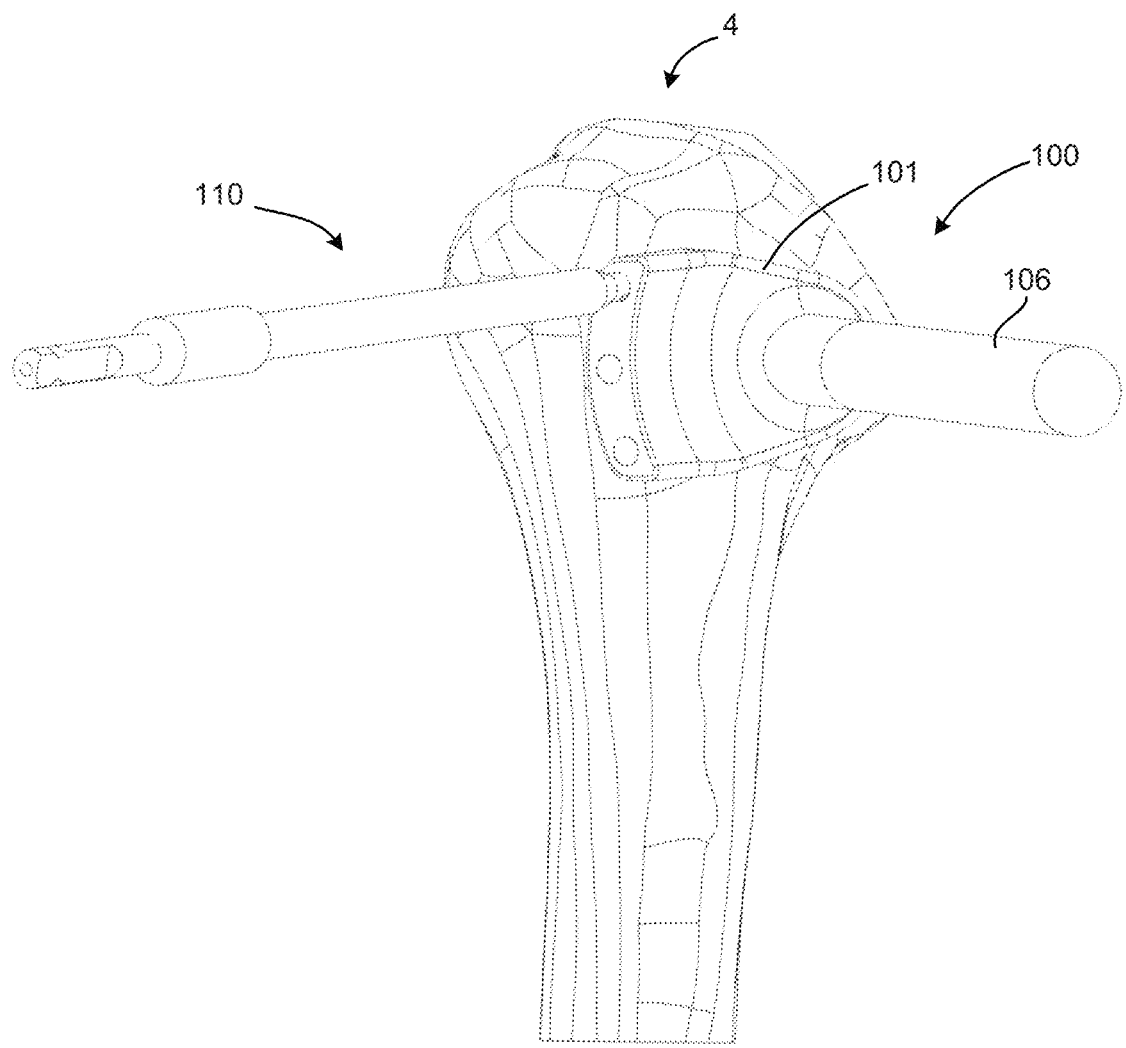
FIG. 22 illustrates a perspective view of the drill guide of FIG. 21 engaged with a bone and a drill tool forming a bone tunnel in the bone.
Figure 23:
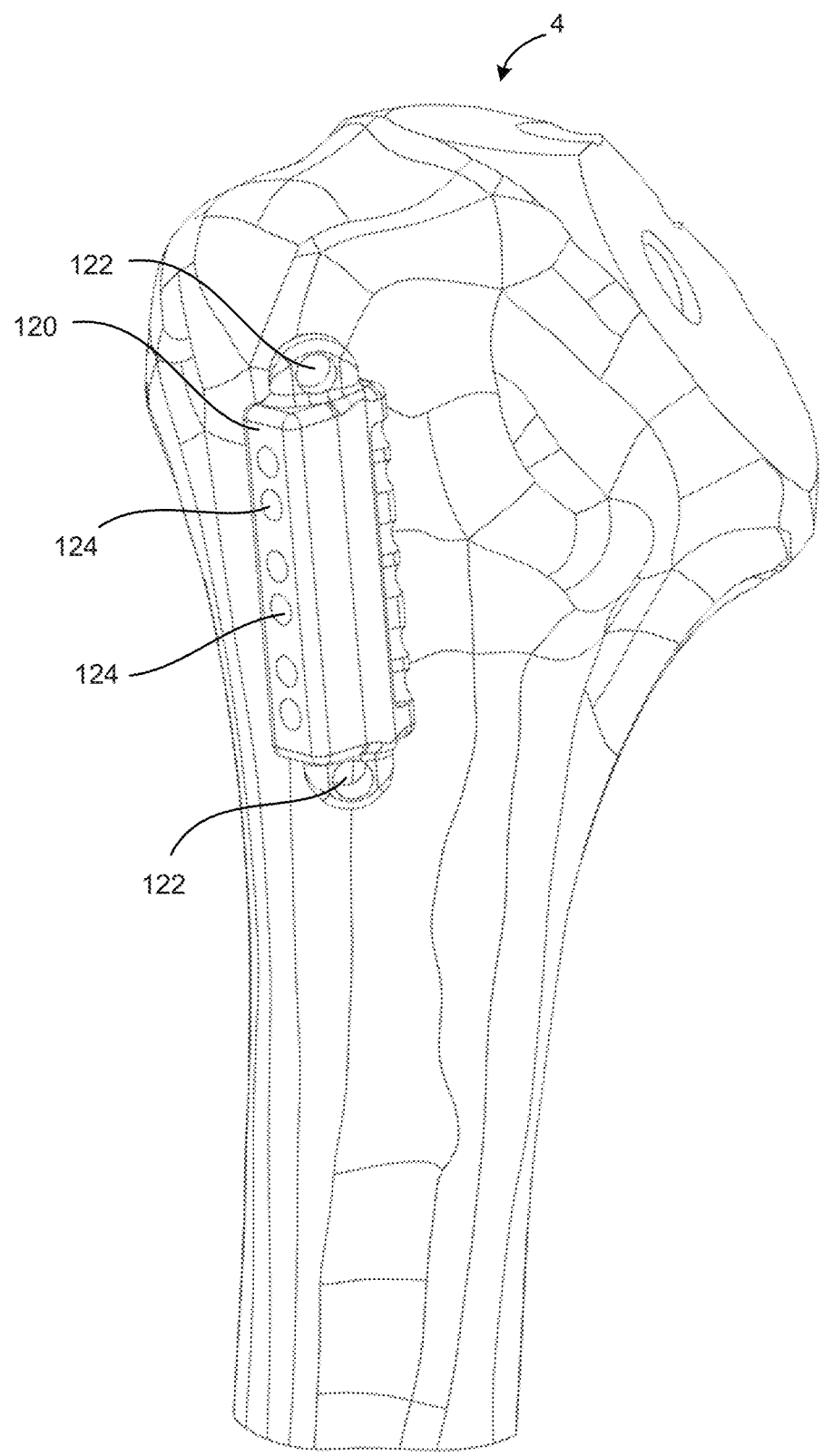
FIG. 23 illustrates a perspective view of a drill guide engaged with a bone, according to another embodiment of the present disclosure.
Figure 24:
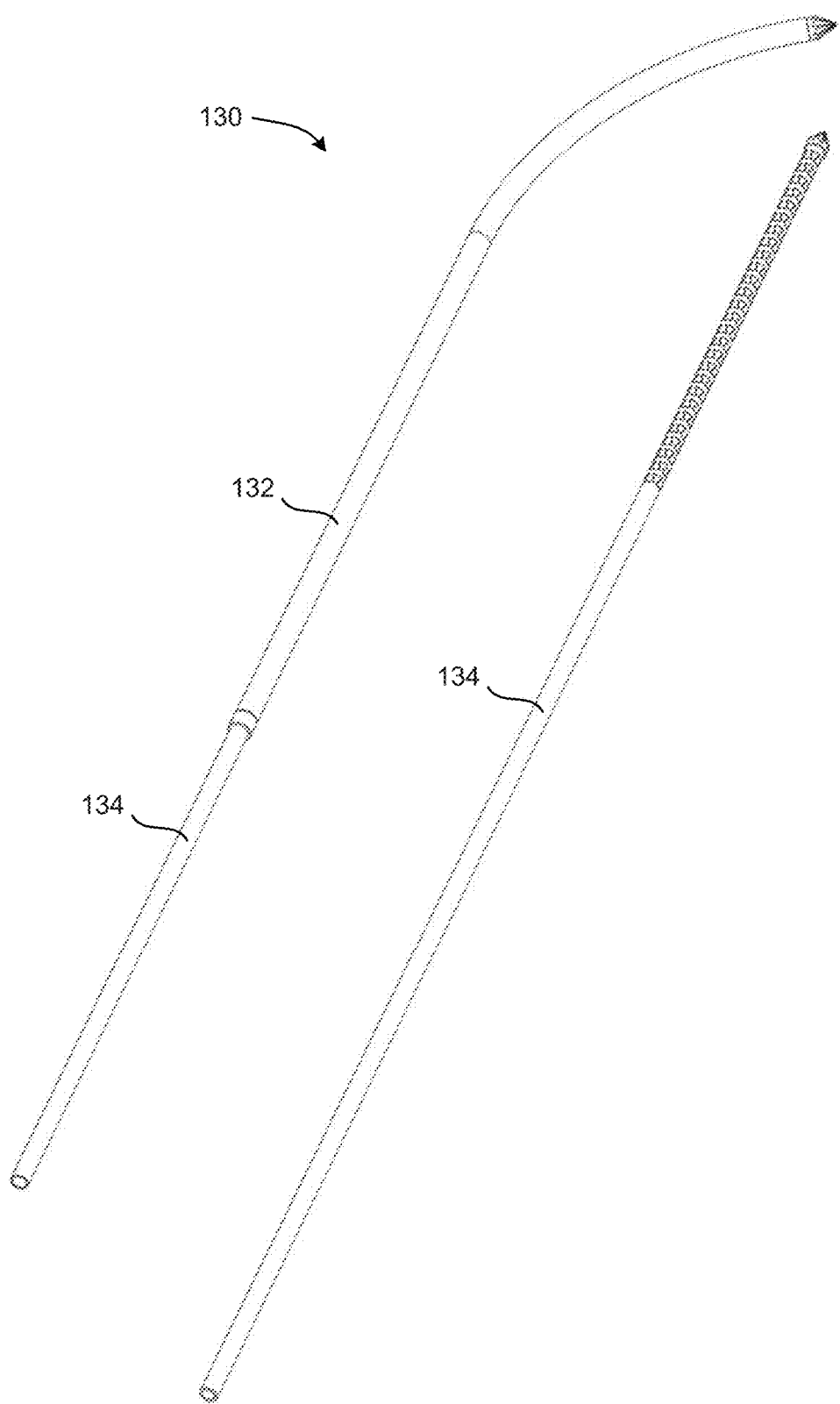
FIG. 24 illustrates a perspective view of a curved drill tool, according to an embodiment of the present disclosure.
Figure 25:
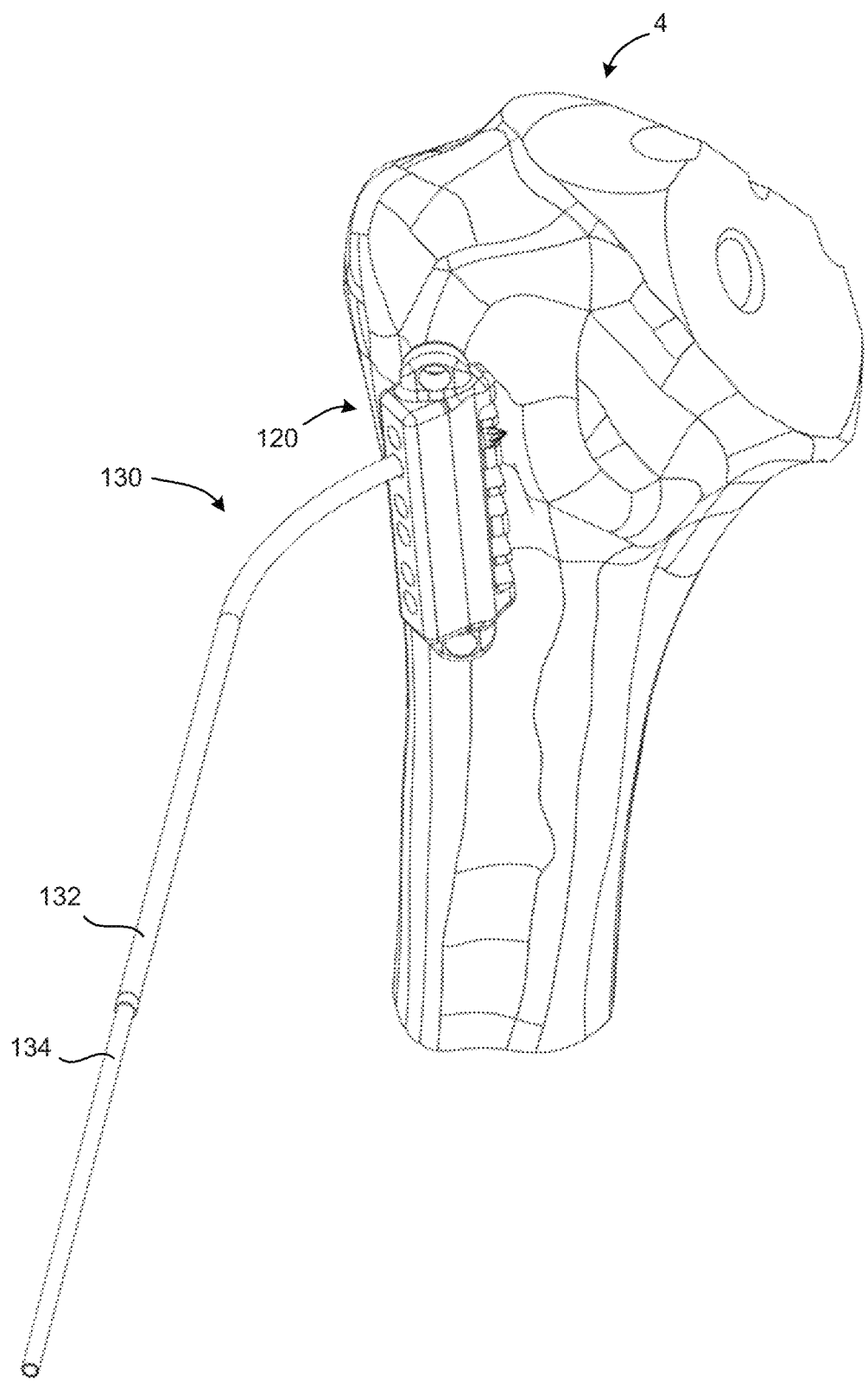
FIG. 25 illustrates a perspective view of the drill guide of FIG. 23 with the curved drill tool of FIG. 24 placed therethrough to form a bone tunnel in the bone.
Figure 26:
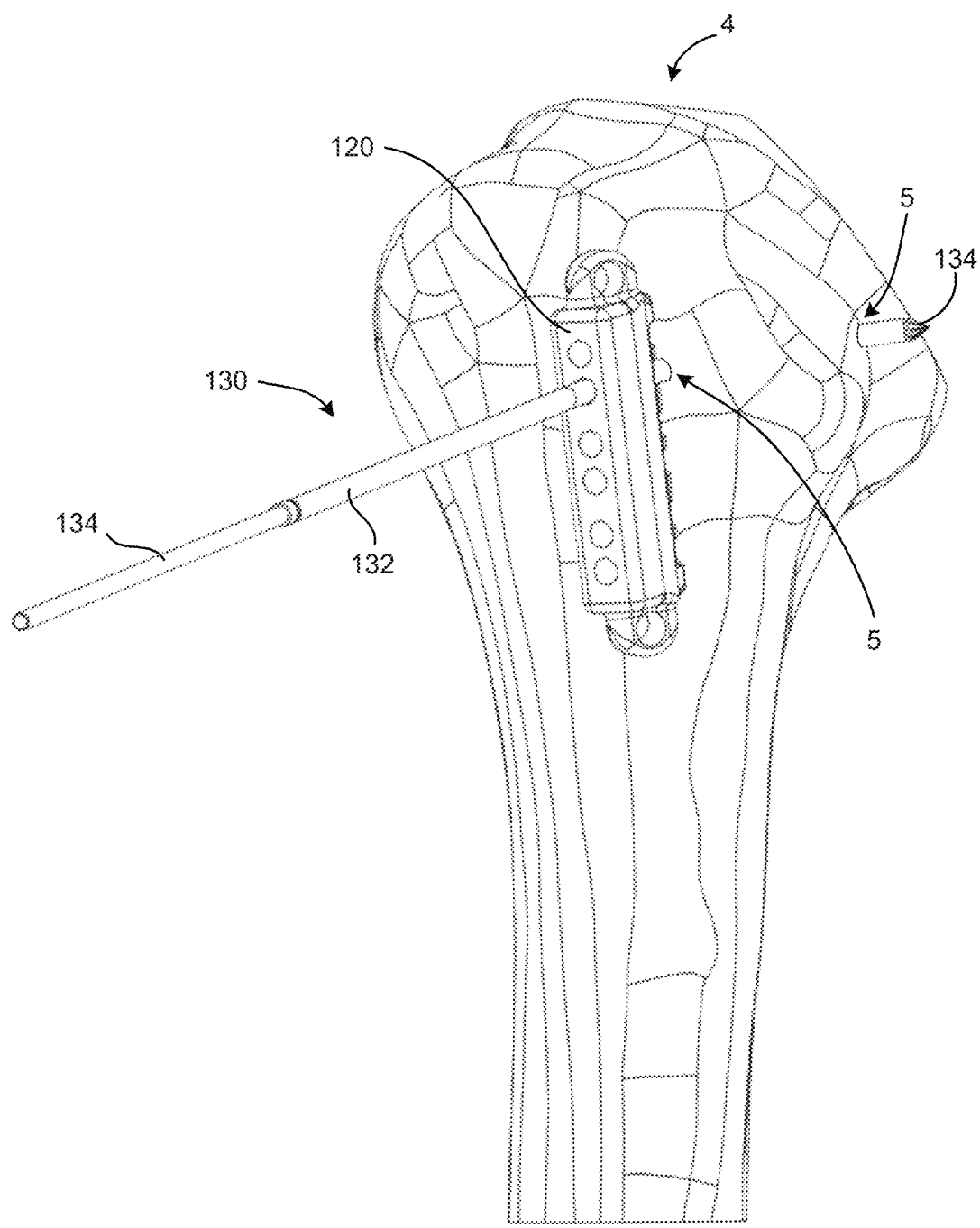
FIG. 26 illustrates another perspective view of the system shown in FIG. 25 with the bone tunnel formed through the bone.
Figure 27:
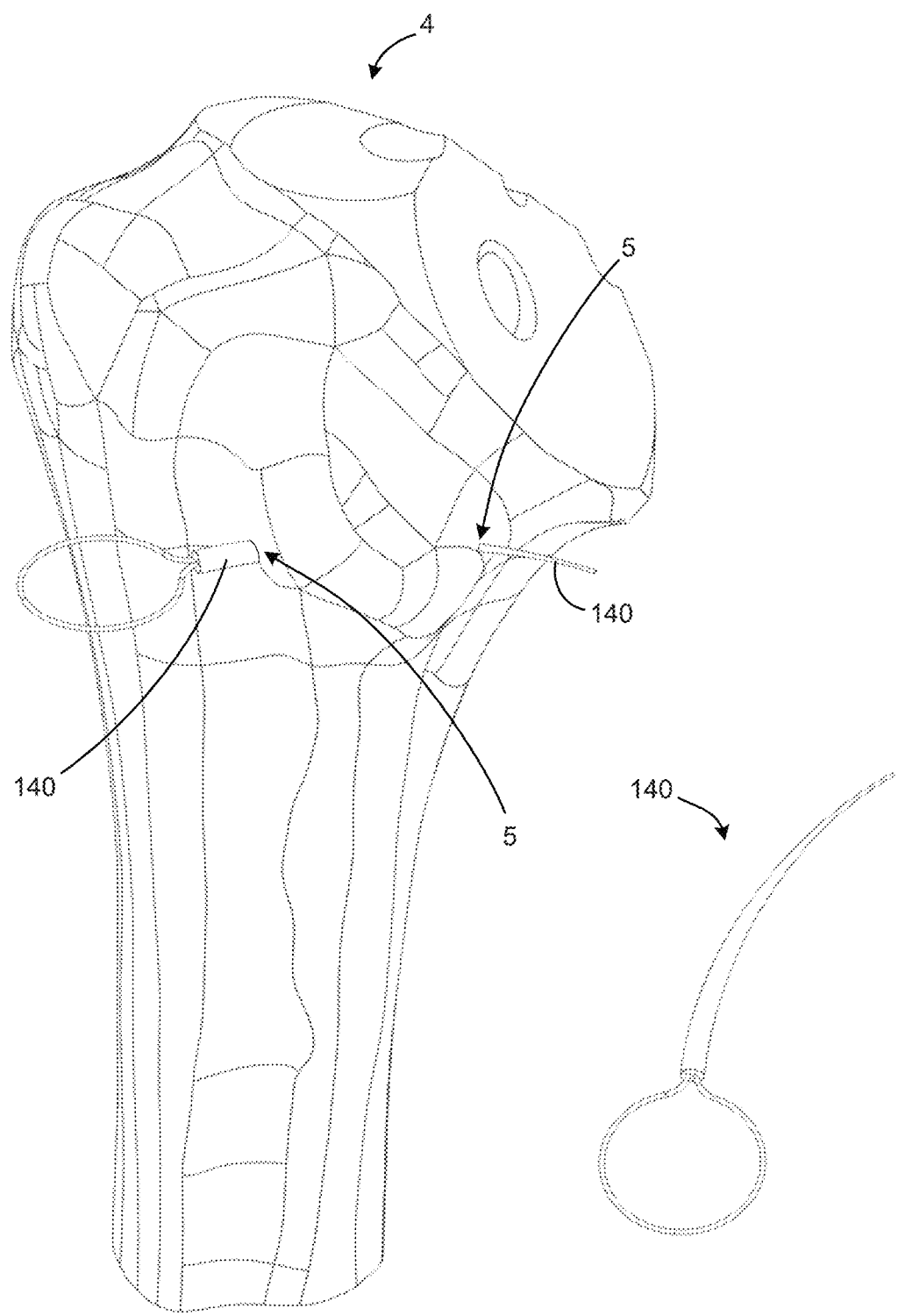
FIG. 27 illustrates a perspective view of a suture passer needle placed through a bone, according to an embodiment of the present disclosure.

FIGS. 17-27 illustrate various instruments and methods for forming the bone tunnel 5 (or multiple bone tunnels) through the bone 4, according to various embodiments of the present disclosure. Specifically, FIG. 17 shows a drill guide 80; FIG. 18 shows the drill guide 80 engaged with the bone 4; FIG. 19 shows a drill guide 90; FIG. 20 shows the drill guide 90 engaged with the bone 4; FIG. 21 shows a drill guide 100; FIG. 22 shows the drill guide 100 engaged with the bone 4 and a drill tool 110 inserted through the drill guide 100 to form the bone tunnel 5; FIG. 23 shows a drill guide 120 engaged with the bone 4; FIG. 24 shows a curved drill tool 130; FIG. 25 shows the curved drill tool 130 placed through the drill guide 120; FIG. 26 shows the curved drill tool 130 forming the bone tunnel 5 through the bone 4; and FIG. 27 shows a suture passer needle 140 placed through the bone 4 to form the bone tunnel 5. The suture passer needle 140 and the drill guides disclosed herein may also be referred to as tunneling devices, guides, or boring tools.

In some embodiments, the tunneling devices may provide an aid/reference for creating bone tunnels that may have specific entry and/or exit points through the bone 4 for fastening the tendon 7 to the bone 4.

In some embodiments, the tunneling devices may be utilized in conjunction with a drill, needle, or other sharp tipped object to create the bone tunnel 5 through the bone 4.

In some embodiments, the tunneling devices may include one or more holes formed on at least one side of the tunneling device. These holes may be utilized to receive a drill or other tunneling tool therethrough.

In some embodiments, the guides may include handles for manipulation and/or features that may reference specific features on the bone 4 that may have been previously prepared as part of a surgical technique for implantation of the prostheses. Additionally, or alternatively, the guides may also include features that reference specific anatomic landmarks. For example, the guides may include an arch, slot, groove, or channel that can conform to the protrusion of the lesser tuberosity. Additionally, or alternatively, the guides may have a protrusion, bump, prominence, or ride that may conform to, or fit within, the channel of a bicipital groove.

In some embodiments, the guides may additionally or alternatively have spikes or other protrusions that may be utilized to help secure the guides to the bone 4 while drilling or tunneling takes place to ensure that the guides remain in place during use.

In some embodiments, the guides may also be secured to the bone 4 or other anatomy by other fixation devices such as fixation pins (not shown).

In some embodiments, the guides may also include design features and/or extensions (not shown) that may aid a surgeon in performing other parts of a surgical procedure, such as performing a humeral head osteotomy, performing a lesser tuberosity osteotomy as part of the subscapularis tendon management process, etc.

In some embodiments, the holes or drill tunnels formed through the guides may be straight or curved to accommodate varying geometries of boring tools.

In some embodiments, the tunneling devices may additionally, or alternatively, include features that may be utilized to create bone tunnels through the bone 4 without the need for drilling. Such tunneling devices may include a single needle, two opposing needles, drills, awls, and/or other boring tools (not shown).

In some embodiments, the boring tools may be actuated from a handle at the working end that drives them into the bone 4. In the example of the tunneling device with two opposing needles (not shown), these two needles may be actuated simultaneously or independently such that they converge at a specific point to form a single continuous bone tunnel in the bone 4.

In some embodiments, the boring tools may be straight or curved such that the formed bone tunnel may comprise a V-shape, an arcuate shape, or may follow a pathway having any other geometrical shape.

In some embodiments, the boring tool(s) may comprise independent components that may be attached to an existing surgical tool, such as a powered tool (e.g., a powered drill, etc.), or a manual tool (e.g., forceps, etc.).

In some embodiments, the bone tunnels may pass underneath the lesser tuberosity of a humeral bone in a generally medial to lateral direction such that one end of the bone tunnel may exit at the bicipital groove. Additionally, or alternatively, the bone tunnels may pass through other locations on the humerus, including but not limited to, one or more of the bone surfaces that may have been previously prepared for the surgical procedure (e.g., see the prepared bone surface 15 shown in FIGS. 28-30).

In some embodiments, the boring tools may include pre-loaded suture so that, as they are passed through the bone 4, they may carry the pre-loaded suture through the bone 4.

In some embodiments, the boring tools may also pass directly through the bone coupler 10 and/or the tendon coupler 20.

In some embodiments, the drill guide 80 shown in FIGS. 17 and 18 may include a drill guide head 81, a drill guide handle 86, one or more guide holes 84 formed through the drill guide head 81, and one or more stabilizing elements 85 projecting from the drill guide head 81.

In some embodiments, the drill guide 90 shown in FIGS. 19 and 20 may include a drill guide head 91, a drill guide handle 96, one or more guide holes 94 formed through the drill guide head 91, and one or more stabilizing elements 95 projecting from the drill guide head 91.

In some embodiments, the drill guide 100 shown in FIGS. 21 and 22 may include a drill guide head 101, a drill guide handle 106, one or more guide holes 104 formed through the drill guide head 101, and one or more stabilizing elements 105 projecting from the drill guide head 101.

In some embodiments, the drill guide 120 shown in FIGS. 23, 25, and 26 may include one or more guide holes 124 to receive a boring tool, and one or more pin holes 122 that may be utilized to secure to the drill guide 120 to the bone 4 with one or more fixation pins (not shown).

In some embodiments, the drill guide 120 may be sized and shaped to sit within or proximate a bicipital groove of a humeral bone and/or reference another anatomical landmark.

In some embodiments, the one or more guide holes 124 may comprise curved trajectories through the drill guide 120 to create curved bone tunnels in the bone 4.

In some embodiments, the curved drill tool 130 shown in FIG. 24 may include a curved sleeve 132 and a flexible drill bit 134 that may be received within the curved sleeve 132.

In some embodiments, the curved sleeve 132 may comprise a fixed rigid outer shaft, and the flexible drill bit 134 may comprise a flexible inner shaft that may drill to an arcuate or non-linear pathway through the bone 4.

In some embodiments, the curved drill tool 130 may be utilized with the drill guide 120 to form the bone tunnel 5 through the bone 4, as shown in FIGS. 25 and 26. In these embodiments, the bone tunnel 5 may comprise a curved bone tunnel.

Figure 31:
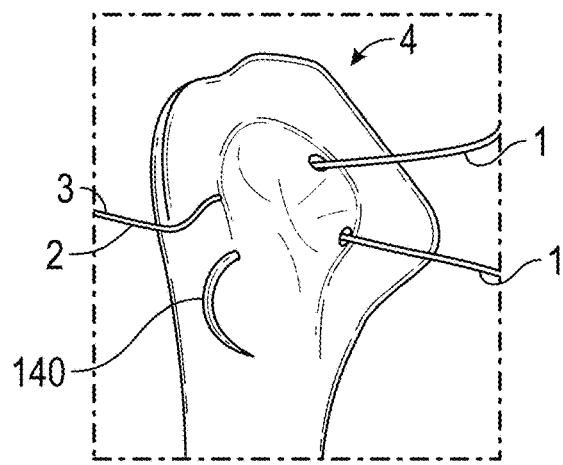
FIG. 31 illustrates a method step for passing a suture through a bone, according to embodiments of the present disclosure.

In some embodiments, the suture passer needle 140 shown in FIGS. 27 and 31 may be utilized to form the bone tunnel 5 through the bone 4 and/or pass a suture through the bone tunnel 5 that is formed by the suture passer needle 140 and/or through a pre-formed bone tunnel in the bone 4.

In some embodiments, the suture passer needle 140 may create a curved, arcuate, or non-linear bone tunnel through the bone and/or pass a suture therethrough.

Figure 28:
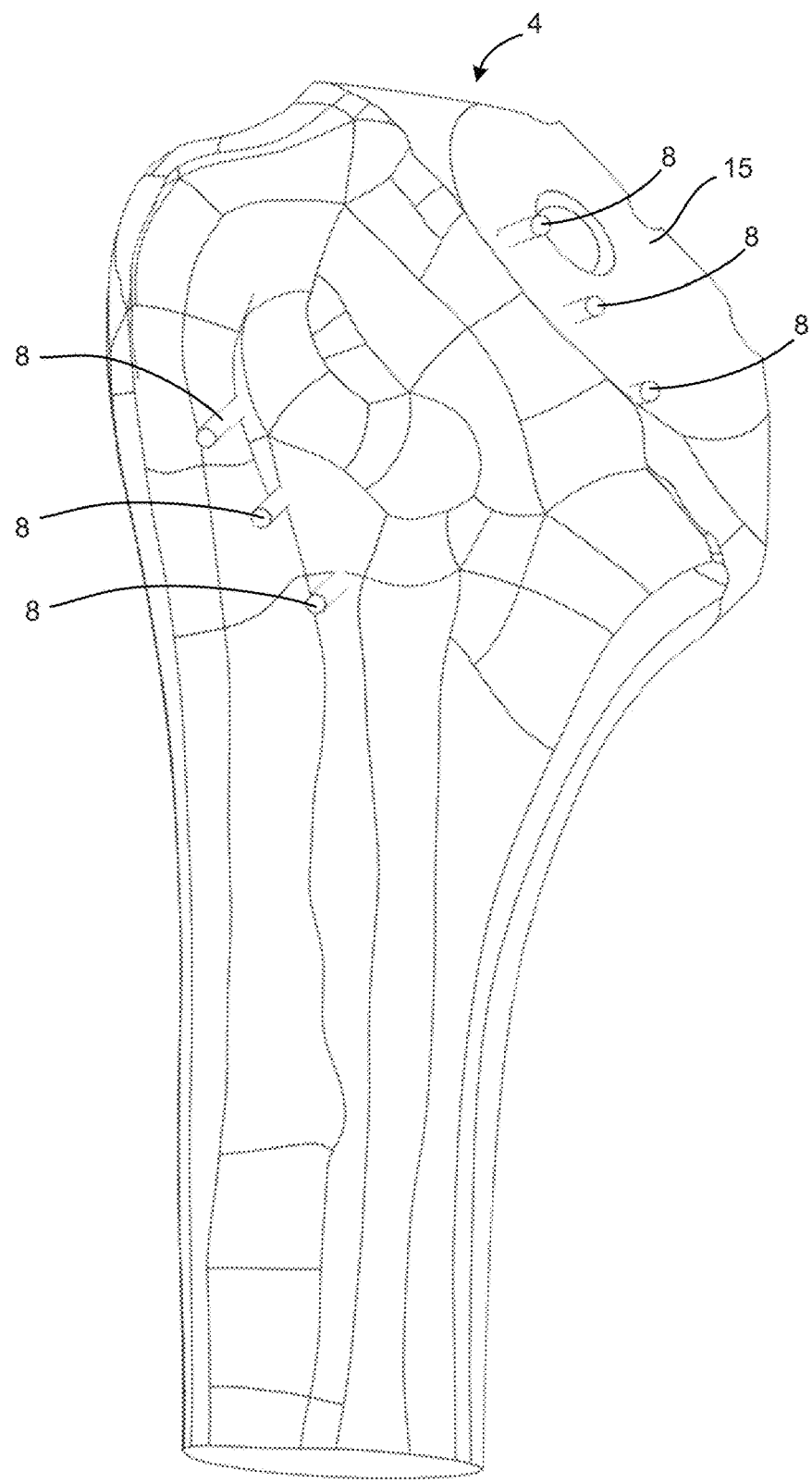
FIG. 28 illustrates a perspective view of a bone with a plurality of sleeves placed therethrough, according to an embodiment of the present disclosure.
Figure 29:
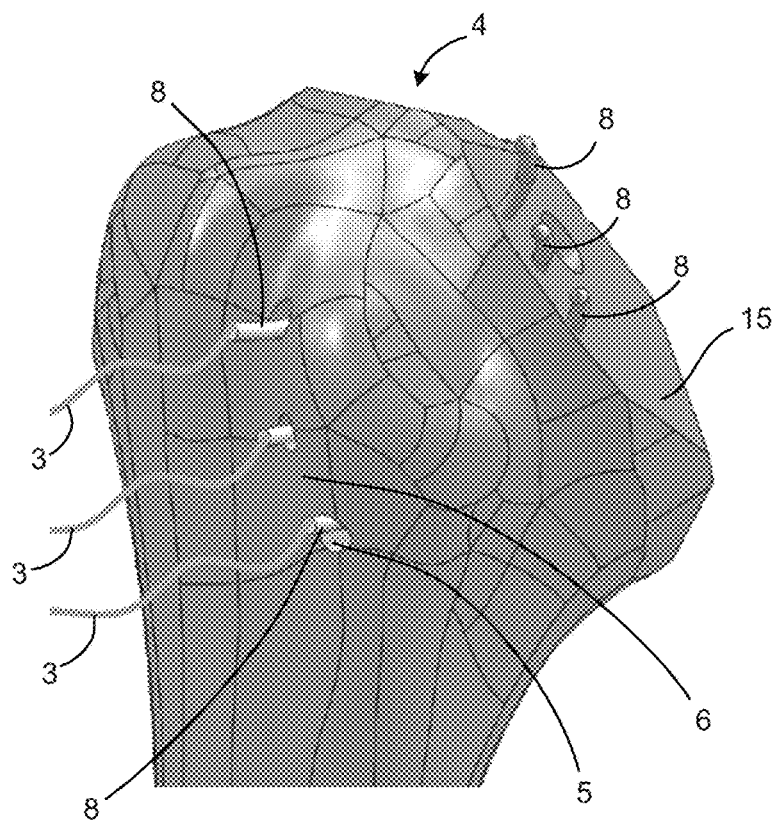
FIG. 29 illustrates another perspective view of the bone and sleeves shown in FIG. 28 with a plurality of sutures inserted into the plurality of sleeves.
Figure 30:
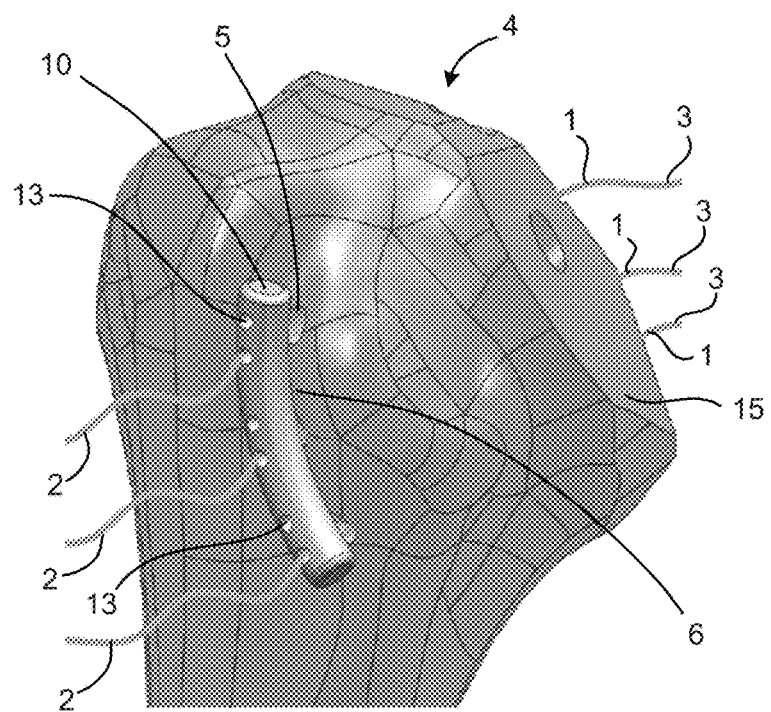
FIG. 30 illustrates a perspective view of the bone coupler of FIG. 12A placed adjacent a bone with plurality of sutures inserted therethrough, according to an embodiment of the present disclosure.

FIGS. 28-30 illustrate various views of a bone 4 with alternative suture pathways that may exit through a prepared bone surface 15 of the bone 4. FIGS. 28 and 29 also include a suture sleeve 8 (or a plurality of suture sleeves) lining these alternative suture pathways. However, it will be understood that the suture sleeve 8 (or plurality of suture sleeves) may be utilized within any bone tunnel described or contemplated herein to reinforce the bone tunnel and help prevent suture migration through the bone 4. In these embodiments, the suture sleeve 8 (or the plurality of suture sleeves) may be utilized in place of, or, in addition to, the bone couplers that are described or contemplated herein to prevent suture migration through the bone 4.

Figure 32:
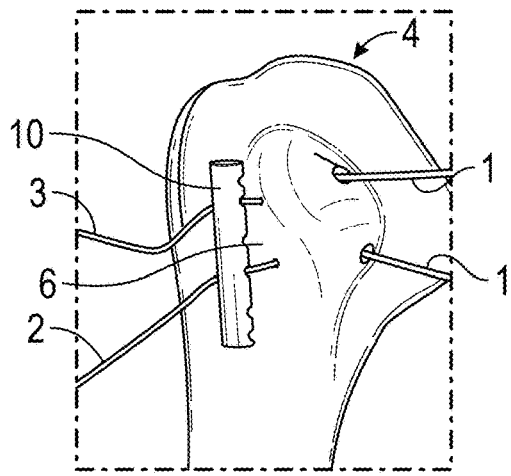
FIG. 32 illustrates another method step for passing a suture through a bone coupler, according to embodiments of the present disclosure.
Figure 33:
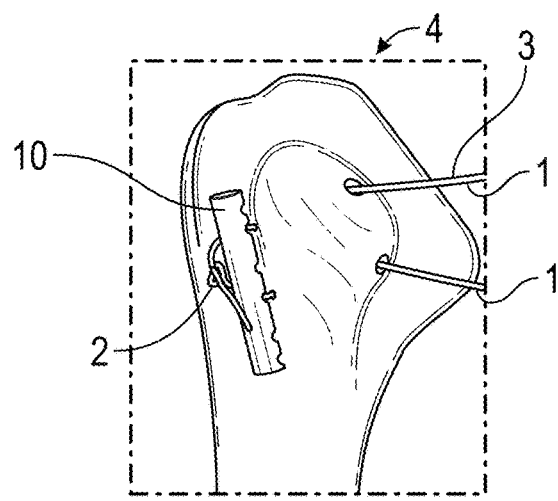
FIG. 33 illustrates another method step for securing a suture to a bone coupler, according to embodiments of the present disclosure.

FIGS. 31-33 illustrate various method steps for passing/securing a suture through a bone and/or other system components of the present disclosure. Specifically, FIG. 31 illustrates a method step for passing a suture through the bone 4; FIG. 32 illustrates another method step for passing the suture through the bone coupler 10; and FIG. 33 illustrates another method step for securing the suture to the bone coupler 10. In this manner, the tendon construct attached to the suture may then be reapproximated to the bone 4 for reattachment thereto.

In some embodiments, a procedure for coupling a tendon to a bone may include preparing one or more bone tunnels through a bone utilizing one or more of the tunneling devices disclosed or contemplated herein in a first step of the procedure. In a second step of the procedure, any of the tendon coupler embodiments disclosed or contemplated herein (or none at all) may be secured to a tendon according to any of the methods disclosed or contemplated herein. In a third step of the procedure, a flexible element, suture, or other stitching material may be passed through the bone tunnels formed in the bone. In a fourth step of the procedure, the flexible element, suture, or other stitching material may be passed through any of the bone coupler embodiments disclosed or contemplated herein (or none at all) according to any of the methods disclosed or contemplated herein. In a fifth step of the procedure, the bone coupler may be secured against the bone. In a sixth step of the procedure, the flexible element, suture, or other stitching material may be tightened to reapproximate the tendon against the bone. In a seventh step of the procedure, the flexible element, suture, or other stitching material may be tied off to complete the tendon repair procedure.

Any procedures or methods disclosed herein may comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the present disclosure. This method of disclosure, however, is not to be interpreted as reflecting an intention that any embodiment requires more features than those expressly recited in that embodiment. Rather, inventive aspects lie in a combination of fewer than all features of any single foregoing disclosed embodiment.

Recitation of the term "first" with respect to a feature or element does not necessarily imply the existence of a second or additional such feature or element. Elements recited in means-plus-function format are intended to be construed in accordance with 35 U.S.C. § 112(f). It will be apparent to those having skill in the art that changes may be made to the details of the above-described embodiments without departing from the underlying principles set forth herein.

The phrases "connected to," "coupled to," "engaged with," and "in communication with" refer to any form of interaction between two or more entities, including mechanical, electrical, magnetic, electromagnetic, fluid, and thermal interaction. Two components may be functionally coupled to each other even though they are not in direct contact with each other. The term "coupled" can include components that are coupled to each other via integral formation, components that are removably and/or non-removably coupled with each other, components that are functionally coupled to each other through one or more intermediary components, etc. The term "abutting" refers to items that may be in direct physical contact with each other, although the items may not necessarily be attached together. The phrase "fluid communication" refers to two or more features that are connected such that a fluid within one feature is able to pass into another feature. As defined herein the term "substantially" means within +/−20% of a target value, measurement, or desired characteristic.

While specific embodiments and applications of the present disclosure have been illustrated and described, it is to be understood that the scope of the present disclosure is not limited to the precise configurations and components disclosed herein. Various modifications, changes, and variations which will be apparent to those skilled in the art may be made in the arrangement, operation, and details of the devices, systems, methods, and/or instruments disclosed herein.

What is claimed is:

1. A system for coupling a tendon to a bone comprising:
   a tendon coupling device comprising a tendon-facing surface engageable with the tendon;
   a fastener configured to secure the tendon to the tendon coupling device;
   a flexible element comprising:
      a first portion; and
      a second portion;
      wherein the first portion of the flexible element is couplable with the fastener to securably attach the flexible element to the tendon; and
   a bone coupling device comprising:
      a bone-facing surface engageable with a surface of the bone proximate a bone tunnel formed through the bone;
      an opposing surface, opposite the bone-facing surface; and
      a hole formed through the bone coupling device intermediate and passing through the bone-facing surface and the opposing surface of the bone coupling device;
      wherein the fastener is configured to pass through the tendon coupling device to secure the tendon coupling device to the tendon; and
      wherein the second portion of the flexible element is receivable through the bone tunnel and the hole to engage the opposing surface of the bone coupling device and securably couple the tendon to the bone.

2. The system of claim 1, wherein the fastener comprises:
   a fastener shaft comprising:
   a first end;
   a second end; and
   a longitudinal passageway formed through the fastener shaft intermediate the first end and the second end;
   a first button coupled to the first end of the fastener shaft; and
   a second button coupled to the second end of the fastener shaft;
   wherein the fastener shaft is configured to penetrate through the tendon and the tendon coupling device to secure the tendon coupling device to the tendon intermediate the first button and the second button; and
   wherein the first portion of the flexible element is receivable through the longitudinal passageway of the fastener shaft to securably attach the flexible element to the tendon.

3. The system of claim 2, wherein the fastener comprises a locking mechanism formed intermediate the fastener shaft and at least one of the first button and the second button and configured to couplably secure the fastener shaft to the at least one of the first button and the second button.

4. The system of claim 1, wherein the fastener comprises a curved fastener comprising:
   a curved fastener shaft comprising:
      a leading end; and
      a trailing end;
   a barbed feature coupled to the leading end; and
   a stop feature coupled to the trailing end;
   wherein the barbed feature is configured to penetrate through the tendon and the tendon coupling device to secure the tendon coupling device to the tendon intermediate the barbed feature and the stop feature; and wherein the first portion of the flexible element is couplable with the fastener to securably attach the flexible element to the tendon.

5. The system of claim 4, wherein the barbed feature comprises:
   a first barbed end;
   a second barbed end; and
   a gap formed intermediate the first barbed end and the second barbed end;
   wherein:
      in a first compressed state, the first barbed end and the second barbed end are configured to compress toward each other; and
      in a second expanded state, the first barbed end and the second barbed end are configured to expand away from each other.

6. The system of claim 1, wherein:
   the tendon-facing surface comprises a first tendon-facing surface;
   the tendon coupling device comprises a second tendon-facing surface, opposite the first tendon-facing surface; and
   the tendon is receivable between the first tendon-facing surface and the second tendon-facing surface of the tendon coupling device to secure the tendon to the tendon coupling device.

7. The system of claim 1, wherein the bone coupling device is integrally formed with the tendon coupling device.

8. A system for coupling a tendon to a bone comprising:
   a tendon coupler comprising a tendon-facing surface engageable with the tendon;
   a first fastener configured to couple the tendon coupler to the tendon;
   a bone coupler coupled to the tendon coupler via integral formation of the bone coupler with the tendon coupler; and
   a second fastener configured to secure the bone coupler to the surface of the bone to securably couple the tendon to the bone.

9. The system of claim 8, wherein:
   the tendon-facing surface comprises a first tendon-facing surface;
   the tendon coupler comprises a second tendon-facing surface, opposite the first tendon-facing surface; and
   the tendon is receivable between the first tendon-facing surface and the second tendon-facing surface of the tendon coupler to secure the tendon to the tendon coupler.

10. The system of claim 8, wherein:
    the first fastener comprises a first portion of a flexible element;
    the second fastener comprises a second portion of the flexible element;
    the bone coupler further comprises:
       an opposing surface, opposite the bone-facing surface; and
       a hole formed through the bone coupler intermediate and passing through the bone-facing surface and the opposing surface of the bone coupler; and
    the bone-facing surface of the bone coupler is engageable with the surface of the bone proximate a bone tunnel formed through the bone;
    wherein:
       the first portion of the flexible element is configured to secure the tendon coupler to the tendon; and
       the second portion of the flexible element is configured to secure the bone coupler to the bone to secure the tendon to the bone.

11. The system of claim 8, wherein the second fastener comprises at least one of:
    a bone staple, a bone screw, and a bone anchor.

12. The system of claim 8, wherein the first fastener comprises:
    a fastener shaft comprising:
       a first end;
       a second end; and
       a longitudinal passageway formed through the fastener shaft intermediate the first end and the second end;
    a first button coupled to the first end of the fastener shaft; and
    a second button coupled to the second end of the fastener shaft;
    wherein the fastener shaft is configured to penetrate through the tendon and the tendon coupler to secure the tendon coupler to the tendon intermediate the first button and the second button, and a first portion of a flexible element is receivable through the longitudinal passageway of the fastener shaft to securably attach the flexible element to the tendon.

13. The system of claim 8, wherein the first fastener comprises a curved fastener comprising:
    a curved fastener shaft comprising:
       a leading end; and
       a trailing end;
    a barbed feature coupled to the leading end; and
    a stop feature coupled to the trailing end;
    wherein the barbed feature is configured to penetrate through the tendon and the tendon coupler to secure the tendon coupler to the tendon intermediate the barbed feature and the stop feature, and a first portion of a flexible element is couplable with the first fastener to securably attach the flexible element to the tendon.

14. A system for coupling a tendon to a bone comprising:
    a tendon connection device comprising a tendon-facing surface engageable with the tendon;
    a flexible element comprising:
       a first portion; and
       a second portion; and
    a bone connection device comprising:
       a bone-facing surface engageable with a surface of the bone proximate a bone tunnel formed through the bone;
       an opposing surface, opposite the bone-facing surface; and
       a hole formed through the bone connection device intermediate and passing through the bone-facing surface and the opposing surface;
       wherein:
          the first portion of the flexible element is configured to wrap around the tendon connection device to couple the tendon connection device to the tendon; and
          the second portion of the flexible element is receivable through the bone tunnel and the hole to engage the opposing surface of the bone connection device and securably couple the tendon to the bone.

15. The system of claim 14, wherein the tendon connection device comprises at least one of: a mesh, a web, a pledget, a pad, and a patch.

16. The system of claim 14, wherein the first portion of the flexible element is configured to weave around the tendon connection device and the tendon to secure the tendon connection device to the tendon.

17. The system of claim 14, wherein:
the tendon-facing surface comprises a first tendon-facing surface;
the tendon connection device comprises a second tendon-facing surface, opposite the first tendon-facing surface; and
the tendon is receivable between the first tendon-facing surface and the second tendon-facing surface of the tendon connection device to secure the tendon to the tendon connection device.

18. The system of claim 14, wherein the tendon connection device is configured to fold around the tendon, and the flexible element is configured to penetrate through the tendon connection device and the tendon to secure the tendon connection device to the tendon.

19. The system of claim 14, wherein the bone connection device is integrally formed with the tendon connection device.

20. A system for coupling a tendon to a bone comprising:
a tendon coupling device comprising a tendon-facing surface engageable with the tendon;
a fastener configured to secure the tendon to the tendon coupling device;
a flexible element comprising:
  a first portion; and
  a second portion;
  wherein the first portion of the flexible element is couplable with the fastener to securably attach the flexible element to the tendon; and
a bone coupling device comprising:
  a bone-facing surface engageable with a surface of the bone proximate a bone tunnel formed through the bone;
  an opposing surface, opposite the bone-facing surface; and
  a hole formed through the bone coupling device intermediate and passing through the bone-facing surface and the opposing surface of the bone coupling device;
  wherein the first portion of the flexible element is configured to pass through the fastener to securably attach the flexible element to the tendon; and
  wherein the second portion of the flexible element is receivable through the bone tunnel and the hole to engage the opposing surface of the bone coupling device and securably couple the tendon to the bone.

21. The system of claim 20, wherein the fastener comprises:
a fastener shaft comprising:
  a first end;
  a second end; and
  a longitudinal passageway formed through the fastener shaft intermediate the first end and the second end;
a first button coupled to the first end of the fastener shaft; and
a second button coupled to the second end of the fastener shaft;
wherein the fastener shaft is configured to penetrate through the tendon and the tendon coupling device to secure the tendon coupling device to the tendon intermediate the first button and the second button; and
wherein the first portion of the flexible element is receivable through the longitudinal passageway of the fastener shaft to securably attach the flexible element to the tendon.

22. The system of claim 21, wherein the fastener comprises a locking mechanism formed intermediate the fastener shaft and at least one of the first button and the second button and configured to couplably secure the fastener shaft to the at least one of the first button and the second button.

23. The system of claim 20, wherein the fastener comprises a curved fastener comprising:
a curved fastener shaft comprising:
  a leading end; and
  a trailing end;
a barbed feature coupled to the leading end; and
a stop feature coupled to the trailing end;
wherein the barbed feature is configured to penetrate through the tendon and the tendon coupling device to secure the tendon coupling device to the tendon intermediate the barbed feature and the stop feature; and
wherein the first portion of the flexible element is couplable with the fastener to securably attach the flexible element to the tendon.

24. The system of claim 23, wherein the barbed feature comprises:
a first barbed end;
a second barbed end; and
a gap formed intermediate the first barbed end and the second barbed end;
wherein:
  in a first compressed state, the first barbed end and the second barbed end are configured to compress toward each other; and
  in a second expanded state, the first barbed end and the second barbed end are configured to expand away from each other.

* * * * *